(12) United States Patent
Tian et al.

(10) Patent No.: US 12,390,458 B2
(45) Date of Patent: Aug. 19, 2025

(54) THERAPEUTIC COMBINATION OF QUINOLINE DERIVATIVE AND ANTIBODY

(71) Applicant: CHIA TAI TIANQING PHARMACEUTICAL GROUP CO., LTD., Lianyungang (CN)

(72) Inventors: Xin Tian, Nanjing (CN); Chen Shen, Nanjing (CN); Peng Lyu, Nanjing (CN); Xiangjian Wang, Nanjing (CN); Xiquan Zhang, Nanjing (CN); Zheng Liu, Nanjing (CN); Yu Xia, Zhongshan (CN); Xiaoping Jin, Zhongshan (CN); Baiyong Li, Zhongshan (CN); Zhongmin Maxwell Wang, Zhongshan (CN); Baohui Han, Shanghai (CN); Tianqing Chu, Shanghai (CN); Hua Zhong, Shanghai (CN); Rong Li, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 893 days.

(21) Appl. No.: 17/260,398

(22) PCT Filed: Jul. 18, 2019

(86) PCT No.: PCT/CN2019/096540
§ 371 (c)(1),
(2) Date: Jan. 14, 2021

(87) PCT Pub. No.: WO2020/015703
PCT Pub. Date: Jan. 23, 2020

(65) Prior Publication Data
US 2022/0160700 A1 May 26, 2022

(30) Foreign Application Priority Data

Jul. 18, 2018 (CN) .......................... 201810790198.6
Nov. 13, 2018 (CN) .......................... 201811346173.6
Feb. 28, 2019 (CN) .......................... 201910149525.4

(51) Int. Cl.
*A61K 31/4709* (2006.01)
*A61K 39/395* (2006.01)
*A61P 35/00* (2006.01)

(52) U.S. Cl.
CPC ...... *A61K 31/4709* (2013.01); *A61K 39/3955* (2013.01); *A61P 35/00* (2018.01)

(58) Field of Classification Search
CPC .. A61K 31/4709; A61K 39/3955; A61P 35/00
See application file for complete search history.

(56) References Cited

U.S. PATENT DOCUMENTS

| | | | |
|---|---|---|---|
| 9,751,859 B2 | 9/2017 | Chen | |
| 2016/0326138 A1* | 11/2016 | Chen | A61K 31/555 |
| 2019/0263923 A1 | 8/2019 | Jure-Kunkel | |
| 2019/0321466 A1* | 10/2019 | Li | C07K 16/28 |
| 2022/0089742 A1 | 3/2022 | Zhang | |

FOREIGN PATENT DOCUMENTS

| | | | |
|---|---|---|---|
| CN | 106255510 A | 12/2016 | |
| CN | 106632674 A | 5/2017 | |
| CN | 106977602 A | 7/2017 | |
| CN | 107771078 A * | 3/2018 | ........... A61K 31/337 |
| EP | 3939610 A1 | 1/2022 | |
| EP | 3973963 A1 | 3/2022 | |
| EP | 3973964 A1 | 3/2022 | |
| WO | WO 2008/112407 A1 | 9/2008 | |
| WO | WO 2015/088847 A1 | 6/2015 | |
| WO | WO 2017/024465 A1 | 2/2017 | |
| WO | WO-2018036472 A1 * | 3/2018 | ........... A61K 39/395 |
| WO | WO 2020/151759 A1 | 7/2020 | |
| WO | WO 2020/181214 A1 | 9/2020 | |
| WO | WO 2020/187152 A1 | 9/2020 | |
| WO | WO 2020/233602 A1 | 11/2020 | |
| WO | WO 2020/233723 A1 | 11/2020 | |
| WO | WO 2020/239085 A1 | 12/2020 | |
| WO | WO 2020/249018 A1 | 12/2020 | |

OTHER PUBLICATIONS

Machine translation of CN107771078 description section. (Year: 2023).*
Hegde et al., Predictive markers of anti-VEGF and emerging role of angiogenesis inhibitors as immunotherapeutics; Dec. 8, 2017, Seminars in Cancer Biology, 52: 117-124. (Year: 2017).*
Sagiv-Barfi et al., Therapeutic antitumor immunity by checkpoint blockade is enhanced by ibrutinib, an inhibitor of both BTK and ITK , 2015, PNAS, 112(9):E966-72. (Year: 2015).*
Li et al., A real-world study of optimal treatment with anlotinib first-line therapy in advanced hepatocellular carcinoma, 2022, Cancer Management and Research, 14:3037-3046. (Year: 2022).*
International Search Report in International Patent Application No. PCT/CN2019/096540, mailed Oct. 15, 2019 (6 pages).
Han, B., "First-line Combination Treatment Based on Anlotinib," ClinicalTrials.gov, ID No. NCT03628521, Aug. 14, 2018 (8 pages).
Zhang, Y., "Anlotinib Plus Sintilimab for NSCLC Patients with First-Generation EGFR-TKIs Drug Resistance along with T790M Negative," ClinicalTrials.gov, ID No. NCT03765775, Dec. 5-6, 2018 (8 pages).
Extended European Search Report in European Patent Application No. EP 19838501.5, mailed Mar. 17, 2022 (13 pages).

(Continued)

*Primary Examiner* — Daniel E Kolker
*Assistant Examiner* — James Ryland Melchior
(74) *Attorney, Agent, or Firm* — NIXON PEABODY LLP

(57) ABSTRACT

The present application provides a therapeutic combination of a quinoline derivative and an antibody, which comprises an immune checkpoint inhibitor and a tyrosine kinase inhibitor, wherein the tyrosine kinase inhibitor is a compound of formula I or a pharmaceutically acceptable salt thereof. The therapeutic combination in the present application shows good activity against lung tumor and liver tumor.

14 Claims, 6 Drawing Sheets

Specification includes a Sequence Listing.

(56) References Cited

OTHER PUBLICATIONS

Han et al., "Anlotinib as a third-line therapy in patients with refractory advanced non-small-cell lung cancer: a multicentre, randomised phase II trial (ALTER0302)", British Journal of Cancer, 118, pp. 654-661, doi: 10.1038/bjc.2017.478, Feb. 13, 2018 (Feb. 13, 2018).

Zhao et al., "Assessment of nivolumab benefit-risk profile of a 240-mg flat dose relative to a 3-mg/kg dosing regimen in patients with advanced tumors", Annals of Oncology, 28, pp. 2002-2008, May 17, 2017 (May 17, 2017).

\* cited by examiner

THERAPEUTIC COMBINATION OF QUINOLINE DERIVATIVE AND ANTIBODY

REFERENCES TO RELATED APPLICATIONS

The present application is a U.S. national stage of PCT/CN2019/096540, filed on Jul. 18, 2019, which claims the benefit and priority to Chinese Patent No. 201910149525.4 filed with the National Intellectual Property Administration, PRC on Feb. 28, 2019, Chinese Patent No. 201811346173.3 filed with the National Intellectual Property Administration, PRC on Nov. 13, 2018, and Chinese Patent No. 201810790198.6 filed with the National Intellectual Property Administration, PRC on Jul. 18, 2018, which are incorporated herein by reference in their entireties.

The instant application contains a Sequence Listing which has been submitted in ASCII format via EFS-Web and is hereby incorporated by reference in its entirety. Said ASCII copy, created on Jul. 15, 2021, is named 059541-074USPX-SL.txt and is 50,316 bytes in size.

TECHNICAL FIELD

The present application belongs to the technical field of medicines and relates to a combined treatment for combating tumors. In particular, the present application relates to a combination of quinoline-based derivative and an antibody and its use in combating tumors.

BACKGROUND

Tyrosine kinase is a group of enzymes which catalyze the phosphorylation of tyrosine residues in proteins. It plays an important role in intracellular signal transduction, takes part in adjustment, signaling and development of normal cells, and is closely related to proliferation, differentiation, migration and apoptosis of tumor cells. Many receptor tyrosine kinases are associated with tumorigenesis and can be classified into epidermal growth factor receptor (EGFR), platelet-derived growth factor receptor (PDGFR), vascular endothelial growth factor receptor (VEGFR), fibroblast growth factor receptor (FGFR) and the like according to the structure of extracellular domain.

Anlotinib is a quinoline derivative tyrosine kinase inhibitor, which plays a role in influencing tumor angiogenesis and proliferation signaling as a multi-target tyrosine kinase inhibitor (TKI), and its main targets comprise: receptor tyrosine kinase vascular endothelial growth factor receptors (VEGFR) 1-3, epidermal growth factor receptor (EGFR), fibroblast growth factor receptors (FGFR) 1-4, platelet-derived growth factor receptors (PDGFR) α and β, and stem cell factor receptors (SCFR) 7, 8, and 9. A phase II trial showed that anlotinib could improve progression-free survival and provide potential benefit for overall survival (Han B, et al., *Br J cancer.* 2018; 118 (5): 654-661). A multicenter, double-blind, phase III randomized clinical trial showed that anlotinib extended overall survival and progression-free survival in Chinese patients, and this finding showed that anlotinib was well tolerated and was a potential third-line or further treatment for advanced NSCLC patients (Han B, et al., *JAMA Oncol.* 2018 November; 4 (11): 1569-1575).

WO2008112407 disclosed in example 24 a quinoline derivative tyrosine kinase inhibitor 1-[[[4-(4-fluoro-2-methyl-1H-indol-5-yl)oxy-6-methoxyquinolin-7-yl]oxy]methyl]cyclopropylamine and a preparation method thereof, and the inhibitor has a structural formula as shown in formula I:

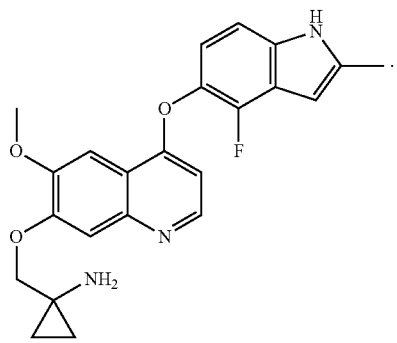 [SMILES: COc1cc2c(Oc3ccc4[nH]c(C)cc4c3F)ccnc2cc1OCC1(N)CC1]

formula I

The innate immune system, which contains T lymphocytes, has a strong anti-cancer capacity featuring broad capacity and precise specificity, thus responding to a variety of tumor antigens. Emerging cancer immunotherapy enhances anti-tumor immune response by adoptive transfer of activated effector cells, immunization against relevant antigens, or providing non-specific immunostimulants. Over the last 20 years, researchers have endeavored to develop specific immune checkpoint inhibitors and expected new immunotherapeutic regimens for the treatment of cancers, including developing antibody ipilimumab (YERVOY®) that binds to and inhibits CTLA-4 for the treatment of patients with advanced melanoma (Hodi et al., (2010) *N Engl J Med* 363: 711-23) and developing antibodies such as nivolumab (Opdivo®) and pembrolizumab (Keytruda®) that specifically bind to programmed death receptor-1 (PD-1) and block the inhibitory PD-1/PD-1 ligand pathway (Topalian et al., (2012a) *N Engl Med* 366: 2443-54). PD-1 (programmed death-1) is a key immune checkpoint receptor expressed by activated T lymphocytes and B lymphocytes and mediates immunosuppression, and its ligands include at least PD-L1 and PD-L2. PD-L1 (programmed death-ligand 1) is also called CD274 or B7-H1, and it is a 40 kDa type-1 transmembrane protein encoded by CD274 gene and is a ligand of PD-1. Both PD-L1 and PD-1 belong to the immunoglobulin superfamily and consist of two extracellular Ig domains, i.e., an N-terminal V domain and a C-terminal constant domain. The binding interface of PD-L1 and programmed death receptor-1 (PD-1) and B7-1 (CD80) is on an IgV-like domain (Lin et al., (2008) *PNAS* 105: 3011-3016). PD-L1 contains a conserved short intracellular tail (about 30 amino acids), and PD-1 contains two cytoplasmic tyrosine-based signaling motifs, namely an immunoreceptor tyrosine-based inhibitory motif (ITIM) and an immunoreceptor tyrosine-based switch motif (ITSM). Following T cell stimulation, PD-1 recruits the tyrosine phosphatase SHP-2 to the ITSM motif in its cytoplasmic tail, resulting in dephosphorylation of effector molecules (such as CD3ζ, PKCθ and ZAP70) involved in the CD3+ T cell signaling cascade (Freeman et al., (2000) *J Exp Med* 192: 1027-34; Latchman et al., (2001) *Nat Immunol* 2: 261-8; Carter et al., (2002) *Eur J Immunol* 32: 634-43). PD-L1 is widely distributed not only on leucocytes and nonhematopoietic cells in lymphoid and non-lymphoid tissues, but also in various cancer cells, and it is highly expressed on the surface of various tumor cells, and the malignant degree and poor prognosis of tumors are closely related to the expression level of PD-L1. Clinical data have suggested that high tumor expression of PD-L1 is associated with increased tumor invasiveness and poor prognosis. The formation of the PD-1/PD-L1 complex transmits inhibitory signals and negatively regulates T cell immune response; it inhibits TCR-mediated T cell activation, cytokine production and T cell proliferation (Fife et al., (2011) *Nature Immunology* 10: 1185-1193), induces exhaustion or anergy among cognate antigen-specific T cells (Hofmeyer et al., (2011) *Journal of Biomedicine and Biotechnology* 2011: 1-9), promotes the differentiation of Th1 cells into Foxp3+ regulatory T cells (Armanath et al., (2011) *Science Trans Med* 3: 1-13; Francisco et al., (2009) *J. Exp. Med.* 206: 3015-3029, and induces apoptosis of effector T cells. Disruption of the PD-L1 gene results in an up-regulated T cell response and the generation of autoreactive T cells (Latchman et al., (2004) *PNAS* 101: 10691-10696). Antibody blockade of PD-1 or PD-L1 results in increased anti-tumor immunity (Iwai et al., (2002) *PNAS* 99: 12293-12297).

The greatest challenge previously encountered in the course of tumor immunotherapy is poor efficacy due to tumor immune tolerance and escape. Therefore, it is important in terms of theoretical significance and application value to break the established immune tolerance of the body to the tumor cells through the combined use of the small-molecule anti-tumor compound and the anti-PD-1/PD-L1 antibody.

SUMMARY

It is an object of the present application to at least provide a therapeutic combination comprising a tyrosine kinase inhibitor and an inhibitor for the interaction between PD-1 and its ligand PD-L1. In some embodiments, the tyrosine kinase inhibitor is a compound of formula I or a pharmaceutically acceptable salt thereof, and in some specific embodiments, the tyrosine kinase inhibitor is a hydrochloride of a compound of formula I, i.e., anlotinib hydrochloride.

In some embodiments, the inhibitor for the interaction between a PD-1 receptor and its ligand PD-L1 is an antibody or an antigen-binding portion thereof that binds to programmed death receptor 1 (PD-1) and/or inhibits PD-1 activity, or an antibody or an antigen-binding portion thereof that binds to programmed death ligand 1 (PD-L1) and/or inhibits PD-L1 activity, e.g., an anti-PD-1 antibody or an anti-PD-L1 antibody. In some specific embodiments, the antibody or the antigen-binding portion thereof is (a) a monoclonal antibody or an antigen-binding fragment thereof that specifically binds to human PD-1 and blocks the binding of human PD-L1 to human PD-1; or (b) a monoclonal antibody or an antigen-binding fragment thereof that specifically binds to human PD-L1 and blocks the binding of human PD-L1 to human PD-1.

In some embodiments, the anti-PD-1 or anti-PD-L1 antibody is an anti-PD-1 or anti-PD-L1 monoclonal antibody. In some embodiments, the anti-PD-1 or anti-PD-L1 antibody is a human or murine antibody.

In some embodiments, the anti-PD-1 antibody may be selected from any one or more of the group consisting of nivolumab, pembrolizumab, durvalumab, toripalimab (JS-001), sintilimab (IBI308), camrelizumab, tislelizumab (BGB-A317), 14C12H1L1 (Akeso Bioscience), genolimzumab (GB226), lizumab (LZM009), HLX-10, BAT-1306, AK103 (HX008), AK104 (Akeso Bioscience), CS1003, SCT-I10A, F520, SG001 and GLS-010.

In some embodiments, the anti-PD-L1 antibody may be selected from any one or more of the group consisting of atezolizumab, avelumab, durvalumab, KL-A167, SHR-1316, BGB-333, JS003, STI-A1014 (ZKAB0011), KN035, MSB2311, HLX-20 and CS-1001.

In some embodiments, the anti-PD-1 antibody comprises:
a heavy chain variable region comprising an amino acid sequence selected from the group consisting of SEQ ID NO: 1, SEQ ID NO: 2, SEQ ID NO: 3, SEQ ID NO: 7, SEQ ID NO: 8, SEQ ID NO: 11, SEQ ID NO: 12, SEQ ID NO: 13, SEQ ID NO: 31, SEQ ID NO: 32 and SEQ ID NO 33 or an amino acid sequence having at least 80% identity, preferably at least 85% identity, more preferably 90%, 91%, 92%, 93%, 94%, 95%, 96%, 97%, 98%, or 99% identity thereto; and
a light chain variable region comprising an amino acid sequence selected from the group consisting of SEQ ID NO: 4, SEQ ID NO: 5, SEQ ID NO: 6, SEQ ID NO: 9, SEQ ID NO: 10, SEQ ID NO: 14, SEQ ID NO: 15, SEQ ID NO: 16, SEQ ID NO: 34, SEQ ID NO: 35 and SEQ ID NO: 36 or an amino acid sequence having at least 80% identity, preferably at least 85% identity, more preferably 90%, 91%, 92%, 93%, 94%, 95%, 96%, 97%, 98% or 99% identity thereto.

In some embodiments, the anti-PD-1 antibody comprises: a heavy chain selected from the group consisting of SEQ ID NO: 17, SEQ ID NO: 37 and SEQ ID NO: 39; and a light chain selected from the group consisting of SEQ ID NO: 18, SEQ ID NO: 40 and SEQ ID NO: 42.

In some embodiments, the anti-PD-1 antibody comprises:
a. a heavy chain variable region set forth in SEQ ID NO: 1 and a light chain variable region set forth in SEQ ID NO: 4;
b. a heavy chain variable region set forth in SEQ ID NO: 2 and a light chain variable region set forth in SEQ ID NO: 5;
c. a heavy chain variable region set forth in SEQ ID NO: 3 and a light chain variable region set forth in SEQ ID NO: 6;
d. a heavy chain variable region set forth in SEQ ID NO: 7 and a light chain variable region set forth in SEQ ID NO: 9;
e. a heavy chain variable region set forth in SEQ ID NO: 8 and a light chain variable region set forth in SEQ ID NO: 10;
f. a heavy chain variable region set forth in SEQ ID NO: 11 and a light chain variable region set forth in SEQ ID NO: 14;
g. a heavy chain variable region set forth in SEQ ID NO: 12 and a light chain variable region set forth in SEQ ID NO: 15;
h. a heavy chain variable region set forth in SEQ ID NO: 13 and a light chain variable region set forth in SEQ ID NO: 16;
i. a heavy chain set forth in SEQ ID NO: 17 and a light chain set forth in SEQ ID NO: 18;
j. a heavy chain variable region set forth in SEQ ID NO: 31 and a light chain variable region set forth in SEQ ID NO: 34;
k. a heavy chain variable region set forth in SEQ ID NO: 32 and a light chain variable region set forth in SEQ ID NO: 35;
l. a heavy chain variable region set forth in SEQ ID NO: 33 and a light chain variable region set forth in SEQ ID NO: 36;
m. a heavy chain set forth in SEQ ID NO: 37 and a light chain set forth in SEQ ID NO: 40;
n. a heavy chain set forth in SEQ ID NO: 38 and a light chain set forth in SEQ ID NO: 41; or
o. a heavy chain set forth in SEQ ID NO: 39 and a light chain set forth in SEQ ID NO: 42.

In some embodiments, the anti-PD-1 antibody is an isolated antibody or antibody fragment that binds to PD-1 and comprises CDR sequences derived from 6F5 antibody, and the CDR sequences of the 6F5 antibody are as follows:

HCDR1:
GFTFSSYG; (SEQ ID NO: 19)

HCDR2:
ISGGGSDT; (SEQ ID NO: 20)

HCDR3:
ARQLNYAWFAY; (SEQ ID NO: 21)

LCDR1:
ESVDNYGISF; (SEQ ID NO: 22)

LCDR2:
TSS; (SEQ ID NO: 23)
and

LCDR3:
QQSKEVPWT. (SEQ ID NO: 24)

In some embodiments, the anti-PD-1 antibody is an isolated antibody or antibody fragment that binds to PD-1 and comprises CDR sequences derived from 14C12 antibody, and the CDR sequences of the 14C12 antibody are as follows:

HCDR1:
GFAFSSYD; (SEQ ID NO: 25)

HCDR2:
ISGGGRYT; (SEQ ID NO: 26)

HCDR3:
ANRYGEAWFAY; (SEQ ID NO: 27)

LCDR1:
QDINTY; (SEQ ID NO: 28)

LCDR2:
RAN; (SEQ ID NO: 29)
and

LCDR3:
LQYDEFPLT. (SEQ ID NO: 30)

In some embodiments, the compound of formula I may be present in the form of a pharmaceutically acceptable salt or a pharmaceutically acceptable formulation thereof, preferably in the form of a hydrochloride thereof.

In some specific embodiments, the compound is 1-[[[4-(4-fluoro-2-methyl-1H-indol-5-yl)oxy-6-methoxyquinolin-7-yl]oxy]methyl]cyclopropylamine hydrochloride, i.e., anlotinib hydrochloride.

In some embodiments, the therapeutic combination comprises: a compound of formula I or a hydrochloride thereof (e.g., dihydrochloride) and sintilimab or an antigen-binding fragment thereof, InVivoMAb anti-mouse PD-1 monoclonal antibody or an antigen-binding fragment thereof or 14C12H1L1 or an antigen-binding fragment thereof.

It is also an object of the present application to at least provide an anti-tumor use of a therapeutic combination comprising a tyrosine kinase inhibitor and an inhibitor for the interaction between PD-1 receptor and its ligand PD-L1. In some embodiments, the tyrosine kinase inhibitor is a compound of formula I or a hydrochloride thereof, and the inhibitor for the interaction between the PD-1 receptor and its ligand PD-L1 is an anti-PD-1 antibody or an anti-PD-L1 antibody or an antigen-binding fragment thereof. In some specific embodiments, the anti-PD-1 monoclonal antibody comprises: a heavy chain variable region having an amino acid sequence selected from the group consisting of SEQ ID NO: 1, SEQ ID NO 2, SEQ ID NO: 3, SEQ ID NO: 7, SEQ ID NO: 8, SEQ ID NO: 11, SEQ ID NO: 12, SEQ ID NO: 13, SEQ ID NO: 31, SEQ ID NO: 32 and SEQ ID NO: 33; and a light chain variable region having an amino acid sequence selected from the group consisting of SEQ ID NO: 4, SEQ ID NO: 5, SEQ ID NO: 6, SEQ ID NO: 9, SEQ ID NO: 10, SEQ ID NO: 14, SEQ ID NO: 15, SEQ ID NO: 16, SEQ ID NO: 34, SEQ ID NO: 35 and SEQ ID NO: 36.

The present application also provides a method for treating an entity having cancer or tumor, which comprises administering to the entity a therapeutically effective amount of a tyrosine kinase inhibitor and a therapeutically effective amount of an inhibitor for the interaction between PD-1 receptor and its ligand PD-L1. In some embodiments, the tyrosine kinase inhibitor is a compound of formula I or a hydrochloride thereof. In some embodiments, the inhibitor for the interaction between PD-1 receptor and its ligand PD-L1 is an antibody or an antigen-binding portion thereof that binds to programmed death receptor 1 (PD-1) and/or inhibits PD-1 activity. For example, the inhibitor is an anti-PD-1 antibody or an anti-PD-L1 antibody or an antigen-binding fragment thereof.

The present application also provides a combination therapy for treating an entity having cancer or tumor, which comprises administering to the entity a therapeutically effective amount of tyrosine kinase inhibitor alone and administering to the entity a therapeutically effective amount of an antibody or an antigen-binding portion thereof alone that inhibits the binding activity of PD-L1 and/or PD-L1.

The present application also provides a method for treating an entity having cancer or tumor, wherein the cancer is lung cancer, and the method comprises: (i) measuring the level of PD-1 and/or PD-L1 in a sample from the entity, wherein the entity is PD-1 and/or PD-L1 positive, and (ii) administering to the entity a therapeutically effective amount of an anti-PD-1 and/or an anti-PD-L1 antibody or an antigen-binding portion thereof.

The present application provides a method for treating an entity having cancer or tumor. In some embodiments, the entity is a patient diagnosed with lung cancer, e.g., a patient diagnosed with non-small cell lung cancer, or a patient diagnosed with small cell lung cancer, which may be refractory, recurrent, or metastatic lung cancer. For example, for some patients, their lung cancer is recurrent; for some patients, the lung cancer is metastatic; for some patients, their lung cancer is refractory. In some specific embodiments, the non-small cell lung cancer described herein is a squamous non-small cell carcinoma, and in other specific embodiments, the non-small cell lung cancer described herein is a non-squamous non-small cell carcinoma. In some specific embodiments, the non-small cell lung cancer described herein is lung adenocarcinoma, squamous cell carcinoma of lung, or large cell lung carcinoma.

In some embodiments of the present application, the entity has previously undergone surgery, chemotherapy, and/or radiation therapy. In some specific embodiments, disease progression recurs after the entity has achieved complete response following surgery, chemotherapy, and/or radiation therapy. In some specific embodiments, the entity has failed to achieve complete response or partial response following surgery, chemotherapy and/or radiation therapy.

In some embodiments of the present application, the entity has not previously received systemic chemotherapy. In some embodiments, the entity has previously received surgical treatment, radiation therapy, induction chemotherapy, and/or adjuvant chemotherapy, or the entity has received concurrent chemotherapy. In some specific embodiments, the entity has not previously received systemic chemotherapy, but has received surgical treatment, radiation therapy, induction chemotherapy and/or adjuvant chemotherapy, or will receive concurrent chemotherapy. In some specific embodiments, disease progression recurs after the entity has achieved complete response following surgical treatment, radiation therapy, induction chemotherapy, concurrent chemotherapy and/or adjuvant chemotherapy. In some specific embodiments, the entity has failed to achieve complete response or partial response following surgical treatment, radiation therapy, induction chemotherapy, concurrent chemotherapy and/or adjuvant chemotherapy. In some specific embodiments, the cancer metastasizes after the entity has undergone surgical treatment, radiation therapy, induction chemotherapy, concurrent chemotherapy and/or adjuvant chemotherapy.

In some embodiments of the present application, the cancer or tumor is lung cancer or malignant lung tumor. In some specific embodiments, the cancer is non-small cell lung cancer (NSCLC). In other specific embodiments, the cancer is small cell lung cancer (SCLC). In some specific embodiments, the cancer is recurrent or refractory lung cancer. In some specific embodiments, the lung cancer is recurrent. In some specific embodiments, the lung cancer is refractory. In some specific embodiments, the lung cancer is metastatic. In some specific embodiments, the cancer treatment is a first-line treatment for recurrent or refractory non-small cell lung cancer. In some specific embodiments, the cancer treatment is a first-line treatment for metastatic non-small cell lung cancer, for example, a first-line treatment for non-small cell lung cancer metastasizing from lymphs, brain and/or bone.

In some embodiments of the present application, the lung cancer is non-small cell lung cancer. In some embodiments, the lung cancer includes squamous lung carcinoma or lung adenocarcinoma. In some specific embodiments, the lung cancer is advanced lung cancer. In some specific embodiments, the lung cancer is EGFR, ALK and/or ROS1 wild-type non-small cell lung cancer. In some specific embodiments, the lung cancer is selected from the group consisting of advanced squamous non-small cell lung cancer and advanced adenocarcinoma non-small cell lung cancer. In some specific embodiments, the lung cancer is selected from the group consisting of i) EGFR, ALK and/or ROS1 wild-type squamous non-small cell lung cancer, and ii) EGFR, ALK and/or ROS1 wild-type adenocarcinoma non-small cell lung cancer. In some embodiments, the lung cancer is advanced (stage IIIB/IV) lung cancer that has failed in a first-line standard chemotherapy or failed to tolerate the chemotherapy.

In some embodiments of the present application, the cancer is recurrent and/or metastatic non-small cell lung cancer. In some embodiments, the cancer is recurrent and/or metastatic small cell lung cancer.

In some embodiments of the present application, the therapeutic combination is used to treat or prevent malignant lung tumor, which can be primary lung tumor or secondary lung tumor.

In some embodiments of the present application, the malignant lung tumor is metastatic lung cancer. In other embodiments, the metastatic lung cancer is metastatic cancer metastasizing from lung cancer, gastric cancer, rectal cancer, colon cancer, colorectal cancer, pancreatic cancer, or breast cancer.

In some embodiments of the present application, the entity is a patient having locally advanced (stage IIIB), metastatic or recurrent (stage IV) NSCLC that is driver gene-negative (i.e., EGFR, ALK, and ROS1 mutation-negative). In some examples, the patient is histologically or cytologically confirmed to be unsuitable for surgery and unable to receive radical concurrent radiotherapy and chemotherapy. In some non-limiting examples, the EGFR mutation includes, but is not limited to, exon 19 or 21 mutation.

In some embodiments of the present application, the therapeutic combination can be used to treat or prevent malignant liver tumor, which can be primary liver tumor or secondary liver tumor.

In some embodiments of the present application, the malignant liver tumor is liver parenchymal cell cancer.

In some embodiments of the present application, the malignant liver tumor is metastatic liver cancer. In other embodiments, the metastatic liver cancer is a metastatic cancer metastasizing from lung cancer, gastric cancer, rectal cancer, colon cancer, colorectal cancer, pancreatic cancer, or breast cancer.

In some embodiments of the present application, the therapeutic combination is a fixed combination. In some embodiments, the fixed combination is in the form of a solid pharmaceutical composition or a liquid pharmaceutical composition.

In some embodiments of the present application, the therapeutic combination is an unfixed combination. In some embodiments, the anti-PD-1/anti-PD-L1 antibody and the compound of formula I in the non-fixed combination are each in the form of a pharmaceutical composition.

In some embodiments, a kit of a therapeutic combination for treating lung tumor or malignant liver tumor is also provided, which comprises (a) a first pharmaceutical composition comprising an anti-PD-1/anti-PD-L1 antibody as an active ingredient; and (b) a second pharmaceutical composition comprising a compound of formula I as an active ingredient.

In some embodiments of the present application, the kit comprises 56-168 mg, such as 84-168 mg, of the compound of formula I. In some embodiments, the kit comprises an amount of the compound of formula I selected from the group consisting of 56 mg, 70 mg, 84 mg, 112 mg, 140 mg, 168 mg and a range formed by any of the aforementioned values. In some embodiments, the kit comprises 112-168 mg of the compound of formula I. In some embodiments, the compounds of formula I within the dose ranges described above may be packaged together as a whole. In other embodiments, the compounds of formula I within the dose ranges described above may be packaged separately in unit doses, e.g., in unit doses of 8 mg, 10 mg or 12 mg.

It is also an object of the present application to provide a method for preventing or treating cancer or tumor, wherein a therapeutically effective amount of a tyrosine kinase inhibitor and a therapeutically effective amount of an inhibitor for the interaction between PD-1 receptor and its ligand PD-L1 are administered (e.g., sequentially or simultaneously) to a subject in need. In some embodiments, the tyrosine kinase inhibitor is a compound of formula I or a hydrochloride thereof. In some embodiments, the inhibitor for the interaction between PD-1 receptor and its ligand PD-L1 is an antibody or an antigen-binding portion thereof that binds to programmed death receptor 1 (PD-1) and/or inhibits PD-1 activity. For example, the inhibitor is an anti-PD-1 antibody or an anti-PD-L1 antibody or an antigen-binding fragment thereof. In some embodiments, the cancer or tumor is selected from a group consisting of liver tumor (e.g., a malignant liver tumor, such as hepatocellular carcinoma) and lung tumor (e.g., lung cancer, such as non-small cell lung cancer).

It is also an object of the present application to at least provide use of an antagonist of PD-1 or PD-L1 in treating cancer, wherein the antagonist is used in combination with a compound of formula I or a pharmaceutically acceptable salt thereof.

It is also an object of the present application to at least provide use of a compound of formula I or a pharmaceutically acceptable salt thereof in treating cancer, wherein the compound is used in combination with an antagonist of PD-1 or PD-L1. In some embodiments, the PD-1 antagonist is a PD-1 monoclonal antibody or an antigen-binding fragment thereof that specifically binds to human PD-1 and blocks the binding of human PD-L1 to human PD-1, and/or the PD-L1 antagonist is a PD-L1 monoclonal antibody or an antigen-binding fragment thereof that specifically binds to human PD-1 and blocks the binding of human PD-L1 to human PD-1.

It is also an object of the present application to at least provide a pharmaceutical pack comprising separately packaged pharmaceutical compositions in separate containers, wherein a pharmaceutical composition comprising a compound of formula I or a pharmaceutically acceptable salt thereof is contained in one container and a pharmaceutical composition comprising a PD-1 antagonist or a PD-L1 antagonist is contained in another container.

In some embodiments of the present application, the pharmaceutical composition comprises 56-168 mg, such as 84-168 mg, of the compound of formula I. In some embodiments, the pharmaceutical composition comprises an amount of the compound of formula I selected from the group consisting of 56 mg, 70 mg, 84 mg, 112 mg, 140 mg, 168 mg and a range formed by any of the aforementioned values. In some embodiments, the pharmaceutical composition comprises 112-168 mg of the compound of formula I.

In some embodiments, the anti-PD-1 antibody is administered at a dose of 1 mg/kg, 2 mg/kg, 3 mg/kg, 5 mg/kg, 6 mg/kg, 9 mg/kg or 10 mg/kg body weight.

In some embodiments, the anti-PD-1 antibody is administered at one or more flat doses capable of effectively treating the cancer. In some specific embodiments, the flat dose is in the range of about 10 mg to about 1000 mg of the anti-PD-1 antibody. In some specific embodiments, the flat dose is selected from the group consisting of about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg and about 1000 mg of the anti-PD-1 antibody. In some specific embodiments, the flat dose is about 200 mg of the anti-PD-1 antibody.

In some embodiments, the treatment with administration of the anti-PD-1 antibody is carried out in a 2-week (14 days) or 3-week (21 days) cycle, and preferably the anti-PD-1 antibody is administered intravenously on the first day (D1) of each cycle. That is, the anti-PD-1 antibody is administered once every two weeks (q2w) or once every three weeks (q3w).

The present application provides an article of manufacture comprising a container containing a fixed dose of an anti-PD-1 antibody. The present application also provides use of an anti-PD-L1 antibody in preparing an article of manufacture for treating cancer comprising a container containing a fixed dose of an anti-PD-1 antibody. In some specific embodiments, the container is a vial. The fixed dose is selected from the group consisting of about 10 mg, about 20 mg, about 30 mg, about 40 mg, about 50 mg, about 60 mg, about 100 mg, about 150 mg, about 200 mg, about 250 mg, about 300 mg, about 350 mg, about 400 mg, about 500 mg and about 1000 mg of the anti-PD-1 antibody. In some specific embodiments, the article of manufacture further comprises a package insert or instructions instructing the user to administer the fixed dose of anti-PD-1 antibody to a cancer patient. In some specific embodiments, the article of manufacture comprises 1 or more than 1 vials containing about 50 mg, 100 mg, 200 mg, 300 mg, 350 mg, 400 mg, 500 mg or 600 mg of the anti-PD-1 antibody. In some specific embodiments, the article of manufacture comprises 1 vial containing about 50 mg of the anti-PD-1 antibody. In some specific embodiments, the article of manufacture comprises 1 vial containing about 200 mg of the anti-PD-1 antibody. In some specific embodiments, the article of manufacture comprises 1 vial containing about 350 mg of the anti-PD-1 antibody. In some specific embodiments, the article of manufacture is packaged as per a 50 mg/5 mL/vial, 100 mg/10 mL/vial, 200 mg/10 mL/vial or 350 mg/35 mL/vial of the anti-PD-1 antibody solution.

It is also an object of the present application to provide a therapeutic combination for the prevention or treatment of cancer or tumor, wherein the therapeutic combination comprises a tyrosine kinase inhibitor and an inhibitor for the interaction between PD-1 and its ligand PD-L1. In some embodiments, the tyrosine kinase inhibitor is a compound of formula I or a hydrochloride thereof. In some embodiments, the inhibitor for the interaction between PD-1 receptor and its ligand PD-L1 is an antibody or an antigen-binding portion thereof that binds to programmed death receptor 1 (PD-1) and/or inhibits PD-1 activity. For example, the inhibitor is an anti-PD-1 antibody or an anti-PD-L1 antibody or an antigen-binding fragment thereof. In some embodiments, the cancer or tumor is selected from a group consisting of liver tumor (e.g., a malignant liver tumor, such as hepatocellular carcinoma) and lung tumor (e.g., lung cancer, such as non-small cell lung cancer).

It is also an object of the present application to provide use of a therapeutic combination in preparing a formulation for the prevention or treatment of cancer or tumor, wherein the therapeutic combination comprises a tyrosine kinase inhibitor and an inhibitor for the interaction between PD-1 and its ligand PD-L1. In some embodiments, the tyrosine kinase inhibitor is a compound of formula I or a hydrochloride thereof. In some embodiments, the inhibitor for the interaction between PD-1 receptor and its ligand PD-L1 is an antibody or an antigen-binding portion thereof that binds to programmed death receptor 1 (PD-1) and/or inhibits PD-1 activity. For example, the inhibitor is an anti-PD-1 antibody or an anti-PD-L1 antibody or an antigen-binding fragment thereof. In some embodiments, the cancer or tumor is selected from a group consisting of liver tumor (e.g., a malignant liver tumor, such as hepatocellular carcinoma) and lung tumor (e.g., lung cancer, such as non-small cell lung cancer).

It is also an object of the present application to provide a unit formulation, wherein the unit formulation comprises: a compound component, 6-12 mg of a compound of formula I or a hydrochloride thereof; and an antibody component, 50-350 mg of an anti-PD-1 antibody or an antigen-binding fragment thereof; wherein the compound component and the antibody component are packaged separately.

It is also an object of the present application to provide a method for preventing or treating cancer or tumor, wherein one or more of the unit formulations described above are administered to a subject in need. Preferably, the compound component and the antibody component in the unit formulation are administered separately.

Pharmaceutical Composition of Anlotinib

In the present application, a pharmaceutical composition of anlotinib is any pharmaceutical composition comprising anlotinib or anlotinib hydrochloride (i.e., the compound of formula I or the hydrochloride thereof) as an active ingredient.

In some embodiments of the present application, the unit dose of the pharmaceutical composition of anlotinib includes 2 mg, 6 mg, 8 mg, 10 mg or 12 mg of anlotinib.

In some embodiments of the present application, according to a treatment cycle of 2 weeks of treatment plus 1 week of interruption, the total dose of the pharmaceutical composition of anlotinib administered per treatment cycle includes 84-168 mg. In some embodiments, the total dose of the pharmaceutical composition of anlotinib includes an amount selected from the group consisting of 84 mg, 112 mg, 140 mg, 168 mg and a range formed by any of the aforementioned values. In some embodiments, the total dose of the pharmaceutical composition of anlotinib preferably includes 112-168 mg.

Anlotinib

As used herein, the chemical name of anlotinib (i.e., the compound of formula I) is 1-[[[4-(4-fluoro-2-methyl-1H-indol-5-yl)oxy-6-methoxyquinolin-7-yl]oxy]methyl]cyclopropylamine, which has the following structural formula:

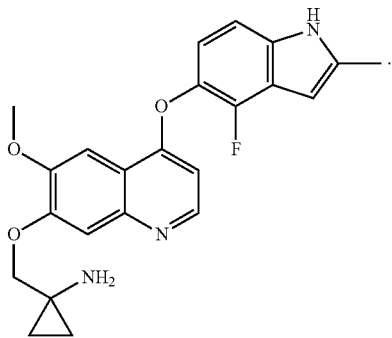

As used herein, the anlotinib includes non-salt forms thereof (for example, free acids or free bases) and further includes pharmaceutically acceptable salts thereof. All the non-salt forms or salts fall within the scope of protection of the present application. For example, the pharmaceutically acceptable salt of anlotinib can be hydrochloride or dihydrochloride. Unless otherwise stated, the dose of anlotinib or a salt thereof involved in present application is calculated based on the free base of anlotinib.

Sintilimab

As used herein, sintilimab (IBI308, IBI-308) is an anti-PD-1 monoclonal antibody, and antibody D of CN108473977A can be referred to for its sequence and structure. On Dec. 27, 2018, the PD-1 antibody drug of Innovent Biologics, namely "sintilimab injection", is approved by the National Medical Products Administration (NMPA) of China to be marketed and used for treating recurrent or refractory classical Hodgkin lymphoma which has been treated with at least second-line systemic chemotherapy.

Full-length sequence of sintilimab's heavy chain:

QVQLVQSGAEVKKPGSSVKVSCKASGGTFSSYAISWVRQAPGQGLEWMGL

IIPMFDTAGYAQKFQGRVAITVDESTSTAYMELSSLRSEDTAVYYCARAE

HSSTGTFDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.

Full-length sequence of sintilimab's light chain:

DIQMTQSPSSVSASVGDRVTITCRASQGISSWLAWYQQKPGKAPKLLISA

ASSLQSGVPSRFSGSGSGTDFTLTISSLQPEDFATYYCQQANHLPFTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

14C12H1L1

As used herein, 14C12H1L1 is an anti-PD-1 monoclonal antibody, and CN106977602A can be referred to for its sequence and structure. In the 14C12H1L1 monoclonal antibody, HCDR1 comprises sequence GFAFSSYD (SEQ ID NO: 25), HCDR2 comprises sequence ISGGGRYT (SEQ ID NO: 26), HCDR3 comprises sequence ANRYGEAW-FAY (SEQ ID NO: 27), LCDR1 comprises sequence QDINTY (SEQ ID NO: 28), LCDR2 comprises sequence RAN (SEQ ID NO: 29), and LCDR3 comprises sequence LQYDEFPLT (SEQ ID NO: 30).

Definitions and Description

Unless otherwise stated, the following terms used in the present application shall have the following meanings. A particular term, unless otherwise specifically defined, should not be considered uncertain or unclear, but construed according to its common meaning in the field. When referring to a trade name, it is intended to refer to its corresponding commercial product, composition or its active ingredient.

As used herein, the term "antibody" refers to an antigen-binding protein having at least one antigen-binding domain. The antibody and the fragment thereof of the present application can be the whole antibody or any fragment thereof. Thus, the antibody and the fragment thereof of the present application includes a monoclonal antibody or a fragment thereof and an antibody variant or a fragment thereof, as well as an immunoconjugate. Examples of the antibody fragment include a Fab fragment, a Fab' fragment, an F(ab)' fragment, an Fv fragment, an isolated CDR region, a single chain Fv molecule (scFv), and other antibody fragments known in the art. The antibody and the fragment thereof may also include a recombinant polypeptide, a fusion protein, and a bispecific antibody. The anti-PD-L1 antibody and the fragment thereof disclosed herein can be of IgG1, IgG2, IgG3, or IgG4 isotype.

The term "isotype" refers to the class of antibodies encoded by the heavy chain constant region gene. In one embodiment, the anti-PD-1/anti-PD-L1 antibody and the fragment thereof disclosed herein are of the IgG1 or IgG4 isotype. The anti-PD-1/anti-PD-L1 antibody and the fragment thereof of the present application can be derived from any species, including but not limited to mouse, rat, rabbit, primate, llama, and human. The PD-1/PD-L1 antibody and the fragment thereof can be a chimeric antibody, a humanized antibody or an intact human antibody.

The term "humanized antibody" refers to an antibody in which the antigen-binding site is derived from a non-human species and the variable region framework is derived from human immunoglobulin sequences. The humanized antibody may comprise substitutions in the framework regions such that the framework may not be an exact copy of the expressed human immunoglobulin or germline gene sequence.

The "isolated antibody" refers to an antibody that is substantially free of other antibodies having different antigenic specificities (e.g., an isolated antibody that specifically binds to PD-1/PD-L1 is substantially free of antibodies that specifically bind to antigens apart from PD-1/PD-L1). However, an isolated antibody that specifically binds to PD-1/PD-L1 may have cross-reactivity with other antigens (such as PD-1/PD-L1 molecules from different species). Furthermore, the isolated antibody may be substantially free of other cellular material and/or chemicals.

The term "monoclonal antibody" ("mAb") refers to an antibody molecule of a single molecule composition. A monoclonal antibody composition exhibits a single binding specificity and affinity for a particular epitope or, in the case of bispecific monoclonal antibody, a dual binding specificity for two different epitopes. The mAb is an example of the isolated antibody. mAbs can be produced by hybridoma techniques, recombinant techniques, transgenic techniques, or other techniques known to those of skill in the art. Examples of isolated anti-PD-1/PD-L1 monoclonal antibodies include, but are not limited to, nivolumab (Opdivo®), pembrolizumab (Keytruda®), durvalumab, avelumab, toripalimab (JS-001, Junshi Biosciences), sintilimab (IBI308, Innovent Biologics), camrelizumab (SHR-1210, Hengrui Medicine, refer to CN105026428B or WO2015085847A1), tislelizumab (BGB-A317, BeiGene), 14C12H1L1 (Akeso Bioscience), genolimzumab (GB226, Genor Biopharma), lizumab (LZM009, Livzon), HLX-10 (Henlius), BAT-1306 (Bio-Thera), HX008 (AK103, Akeso Bioscience/Hanzhong Pharmaceuticals), AK104 (Akeso Bioscience), CS1003 (CStone Pharmaceuticals), SCT-I10A (SinoCellTech), F520 (Shandong New Time Pharmaceutical/Lunan Pharmaceutical Group), SG001 (Sumgen Bio), GLS-010 (Goloria Pharceuticals), atezolizumab (Tecentriq®, Roche), avelumab (Bavencio®, Merck/Pfizer), durvalumab (Imfinzi®, AstraZeneca), KL-A167 (Kelun Pharmaceutical), SHR-1316 (Hengrui Medicine), BGB-333 (BeiGene), JS003 (Junshi Biosciences), STI-A1014 (ZKAB0011, Zhaoke Pharmaceutical), KN035 (Alphamab Oncology/3D Medicines), MSB2311 (Mabspace Biosciences), HLX-20 (Henlius), CS-1001 (CStone Pharmaceuticals), etc.

An "antigen-binding portion" (also referred to as an "antigen-binding fragment") of an antibody refers to one or more fragments of the antibody that retain the ability to specifically bind to an antigen bound to by an intact antibody.

As used herein, the term "derived", when used to refer to a molecule or polypeptide relative to a reference antibody or other binding proteins, means a molecule or polypeptide that is capable of specifically binding to the same epitope as the reference antibody or other binding proteins.

As used herein, the term "EC50" refers to the effective concentration, 50% of the maximal response of an antibody. As used herein, the term "IC50" refers to the inhibitory concentration, 50% of the maximal response of an antibody. Both EC50 and IC50 can be measured by ELISA or FACS analysis or any other method known in the art.

The term "treatment" usually refers to operations for acquiring needed pharmacological effect and/or physiological effect. In term of fully or partially preventing a disease or a symptom thereof, the effect can be preventive; and/or in term of partially or fully stabilizing or curing the disease and/or a side effect of the disease, the effect can be therapeutic. "Treatment" used therein encompasses any treatment to a disease in a patient, including (a) preventing a disease or a symptom that has not been confirmed in a susceptible patient; (b) inhibiting a symptom of a disease, i.e., blocking the progression of the disease; or (c) alleviating a symptom of a disease, i.e., causing remission of a disease or a symptom.

As used herein, the term "general treatment" refers to treatment in which a drug substance is transported through the bloodstream to reach and affect cells of the whole body.

As used herein, the term "systemic chemotherapy" refers to general chemotherapy that excludes chemotherapy for locally advanced disease as one of the links of multimodal treatment, wherein the chemotherapy for locally advanced disease includes induction chemotherapy, concurrent chemotherapy with radiotherapy, and adjuvant chemotherapy.

As used herein, the term "subject" means a mammal, such as a rodent, feline, canine, and primate. Preferably, the subject according to the present application is a human.

"Administering" means physically introducing the composition comprising the therapeutic agent to the entity using any of a variety of methods and delivery systems known to those skilled in the art. Routes of administration of immune checkpoint inhibitors (e.g., an anti-PD-1 antibody or an anti-PD-L1 antibody) include intravenous, intramuscular, subcutaneous, intraperitoneal, spinal, or other parenteral routes of administration, for example, by injection or infusion. As used herein, the phrase "parenteral administration" refers to modes of administration apart from enteral and local administration, typically by injection, including, but are not limited to, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion and in vivo electroporation. In some embodiments, the immune checkpoint inhibitor (e.g., an anti-PD-1 antibody or an anti-PD-L1 antibody) is administered by a non-parenteral route, and in some embodiments, it is administered orally. Other non-parenteral routes include local, epidermal or mucosal routes of administration, for example, administrating intranasally, vaginally, rectally, sublingually or locally. Administration may also be performed, e.g., once, multiple times, and/or over one or more extended periods of time.

As used herein, an "adverse event" (AE) is any adverse and often unintended or undesirable sign (including abnormal laboratory findings), symptom, or disease associated with the use of medical therapy. For example, an adverse event may be associated with activation of the immune system or expansion of immune system cells (e.g., T cells) in response to treatment. The medical treatment may have one or more related AEs, and each AE may have the same or a different severity level. Reference to a method capable of "altering an adverse event" refers to a treatment regimen that reduces the incidence and/or severity of one or more AEs associated with the use of a different treatment regimen.

As used herein, "administration interval" refers to the amount of time that elapses among multiple doses of a formulation disclosed herein administered to an entity. The administration interval may thus be indicated as a range.

As used herein, the term "administration frequency" refers to the frequency at which doses of a formulation disclosed herein are administered over a given time. The administration frequency may be indicated as the number of administrations per given time, e.g., once every week or once every two weeks.

The term "flat dose" refers to a dose administered to a patient without considering the weight or the body surface area (BSA) of the patient. Thus, the flat dose is specified as the absolute amount of a medicament (e.g., anti-PD-1 antibody) rather than the mg/kg dose. For example, a 60 kg human and a 100 kg human will receive the same dose of antibody (e.g., 240 mg of anti-PD-1 antibody).

The term "fixed dose" in reference to a composition of the present application means that two or more different antibodies in a single composition are present in the composition in a specific (fixed) ratio to each other. In some embodiments, the fixed dose is based on the weight of the antibody (e.g., mg). In some embodiments, the fixed dose is based on the concentration of the antibody (e.g., mg/mL). In some embodiments, the ratio of mg first antibody to mg second antibody is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1. For example, a 3:1 ratio of a first antibody and a second antibody may refer to that a vial may contain about 240 mg of the first antibody and 80 mg of the second antibody, or about 3 mg/mL of the first antibody and 1 mg/mL of the second antibody.

The term "weight-based dose" mentioned herein refers to a dose calculated based on the weight of a patient and administered to the patient. For example, when a patient weighing 60 kg requires 3 mg/kg of anti-PD-1 antibody and 1 mg/kg of anti-CTLA-4 antibody, one can extract appropriate amounts of anti-PD-1 antibody (i.e., 180 mg) and anti-CTLA-4 antibody (i.e., 60 mg) at a time from a 3:1 fixed-dose formulation of anti-PD-1 antibody and anti-CTLA-4 antibody.

The term "immunotherapy" refers to the treatment of an entity with a disease or at risk of infection or relapse of a disease by a method that comprises inducing, enhancing, suppressing or otherwise altering an immune response. The "treatment" or "therapy" for an entity refers to any type of intervention or procedure performed on the entity or the administration of an active agent to the entity, with the purpose of reversing, alleviating, ameliorating, inhibiting, slowing or preventing the onset, progression, development, severity or recurrence of a symptom, complication, or condition, or biochemical indicators associated with the disease.

As used herein, "PD 1/PD-L1 positive" may be used interchangeably with "at least about 1% PD-1/PD-L1 expression". In one embodiment, PD-1/PD-L1 expression may be used by any method known in the art. In another embodiment, PD-1/PD-L1 expression is measured by automated IHC. In some embodiments, "PD-1/PD-L1 positive" refers to the presence of at least 100 cells expressing PD-1/PD-L1 on the cell surface. "Programmed death receptor-1 (PD-1)" refers to an immunosuppressive receptor belonging to the CD28 family. PD-1 is expressed primarily on previously activated T cells in vivo and binds to two ligands PD-L1 and PD-L2. As used herein, the term "PD-1" includes human PD-1 (hPD-1), variants, homologs and species homologs of hPD-1, and analogs having at least one common epitope with hPD-1.

"Programmed death ligand-1 (PD-L1)" is one of two cell surface glycoprotein ligands for PD-1 (the other is PD-L2), which down-regulates T cell activation and cytokine secretion upon binding to PD-1.

"Entity" includes any human or non-human animal. The term "non-human animal" includes, but is not limited to, vertebrates such as non-human primates, sheep, dogs, and rodents such as mice, rats and guinea pigs. In some embodiments, the entity is a human. The terms "entity," "subject" and "patient" can be used interchangeably herein in certain contexts.

A "therapeutically effective amount" or "therapeutically effective dose" of a drug or therapeutic agent is any amount of a drug that, when used alone or in combination with another therapeutic agent, protects an entity from the onset of a disease or promotes disease regression as evidenced by reduction in the severity of disease symptoms, increase in the frequency and duration of disease symptom-free stage, or the prevention of damage or disability caused by the affliction of the disease. The ability of a therapeutic agent to promote disease regression can be evaluated using a variety of methods known to skilled practitioners, such as in a human entity during clinical trials, in an animal model system that predicts efficacy for humans, or by determining the activity of the drug in an in vitro assay.

As used herein, a "sub-therapeutic dose" refers to a dose of a therapeutic compound (e.g., an antibody) that is less than its usual or typical dose when administered alone for the treatment of a hyperproliferative disease (e.g., cancer).

As an example, an "anti-cancer drug" promotes cancer regression in an entity or prevents further tumor growth. In some embodiments, the therapeutically effective amount of the drug promotes the cancer regression to the point of eliminating the cancer. "Promoting cancer regression" means that the administration of an effective amount of a drug, alone or in combination with an anti-neoplastic agent results in a reduction of tumor growth or size, necrosis of the tumor, reduction in the severity of at least one disease symptom, increase in the frequency and duration of disease symptom-free stage, or the prevention of damage or disability caused by the affliction of the disease. Furthermore, the terms "effective" and "effectiveness" with respect to treatment include pharmacological effectiveness and physiological safety. Pharmacological effectiveness refers to the ability of a drug to promote cancer regression in a patient. Physiological safety refers to the level of toxicity or other adverse physiological effects (adverse effects) at the cellular, organ and/or organism level resulting from drug administration.

As an example for treating a tumor, a therapeutically effective amount of an anti-cancer agent can inhibit cell growth or tumor growth by at least about 10%, at least about 20%, at least about 40%, at least about 60%, or at least about 80% relative to an untreated entity, or, in some embodiments, relative to a patient treated with standard of care therapy. In other embodiments of the present application, tumor regression may be observed for a period of at least about 20 days, at least about 40 days, or at least about 60 days. Despite these final measurements of therapeutic effectiveness, the evaluation of immunotherapeutic drugs must also take into account "immune-related" response patterns.

An "immune-related" response pattern refers to the clinical response pattern often observed in cancer patients treated with an immunotherapeutic agent that produces an anti-tumor effect by inducing a cancer-specific immune response or by altering the innate immune process. This response pattern is characterized by beneficial therapeutic effects following an initial increase in tumor burden or the appearance of new lesions, which would be classified as disease progression and would be synonymous with drug failure in the evaluation of traditional chemotherapeutic agents. Thus, proper evaluation of immunotherapeutic agents may require long-term monitoring of the effect of these agents on target disease.

A therapeutically effective amount of a drug includes a "prophylactically effective amount", which is any amount of a drug that inhibits the occurrence or recurrence of cancer when administered, alone or in combination with an anti-neoplastic agent, to an entity at risk of developing cancer (e.g., an entity having a premalignant condition) or an entity at risk of recurrence of cancer. In some embodiments, the prophylactically effective amount completely prevents the occurrence or recurrence of cancer. "Inhibiting" the occurrence or recurrence of cancer means reducing the possibility of the occurrence or recurrence of cancer or completely preventing the occurrence or recurrence of cancer.

A "recurrent" cancer is one that regenerates at the initial site or a distant site after being responsive to initial treatment (e.g., surgery). A "locally recurrent" cancer is one that occurs, after treatment, at the same location as the previously treated cancer.

A "unresectable" cancer is one that cannot be removed by surgery.

A "metastatic" cancer refers to one that spreads from one part of the body (e.g., the lung) to another part of the body.

The use of alternatives (e.g., "or") shall be understood to refer to any one, two, or any combination of the alternatives. As used herein, the indefinite articles "a" or "an" shall be understood to mean "one or more" of any listed or enumerated components.

The terms "about", "approximately" or "substantially comprise" refers to a value or composition within an acceptable error range for the particular value or composition as determined by one of ordinary skill in the art, which will depend in part on how the value or composition is measured or determined, i.e., the limitations of the measurement system. For example, "about", "approximately" or "substantially comprise" may refer to being within 1 or more than 1 standard deviation as practiced in the art. Alternatively, "about" or "substantially comprises" may refer to a range that differs by up to 10% or 20% (i.e., ±10% or ±20%) from the parameter or value modified thereby. For example, about 3 mg may include any number between 2.7 mg and 3.3 mg (for 10%) or between 2.4 mg and 3.6 mg (for 20%). Furthermore, particularly with respect to biological systems or processes, the term may refer to being up to an order of magnitude or up to at most 5 times the numerical value. When a particular value or composition is provided in the present application and claims, unless otherwise stated, the meaning of "about" or "substantially comprise" should be assumed to be within an acceptable error range of the particular value or composition.

As used herein, the term "about once every week", "about once every two weeks" or any other similar administration interval term refers to an approximation. "About once every week" may include once every 7±1 days, i.e., once every 6 days to once every 8 days. "About once every two weeks" may include once every 14±3 days, i.e., once every 11 days to once every 17 days. Similar approximations apply to, for example, about once every 3 weeks, about once every 4 weeks, about once every 5 weeks, about once every 6 weeks, and about once every 12 weeks. In some embodiments, an administration interval of about once every 6 weeks or about once every 12 weeks means that a first dose may be administered on any day of the first week, and then a second dose may be administered on any day of the sixth or twelfth week, respectively. In other embodiments, an administration interval of about once every 6 weeks or about once every 12 weeks means that a first dose is administered on a particular day (e.g., Monday) of the first week and then a second dose is administered on the same day (e.g., Monday) of the sixth or twelfth week, respectively. Similar principles apply to phrases including but not limited to, "about once every 2 weeks", "about once every month", etc.

As used herein, unless otherwise indicated, any concentration range, percentage range, ratio range, or integer range shall be understood as including the value of any integer within the listed range and including, when appropriate, fractions thereof (such as one tenth and one hundredth of the integer).

Unless otherwise stated, "about" or "approximately" in present application means being within ±5%, preferably within ±2%, and more preferably within ±1% of the specified numerical range given. For example, a pH of about 5.5 means a pH of 5.5±5%, preferably a pH of 5.5±2%, and more preferably a pH of 5.5±1%.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" includes salts formed by basic radicals and free acids and salts formed by acidic radicals and free bases, for example, hydrochloride, hydrobromide, nitrate, sulfate, phosphate, formate, acetate, trifluoroacetate, fumarate, oxalate, maleate, citrate, succinate, mesylate, benzenesulfonate and p-methylbenzenesulfonate, preferably, hydrochloride, hydrobromide, sulfate, formate, acetate, trifluoroacetate, fumarate, maleate, mesylate, p-methylbenzenesulfonate, sodium salt, potassium salt, ammonium salt, amino acid salt, etc. In the present application, when forming a pharmaceutically acceptable salt, the free acid and the basic radical are in a molar weight ratio of about 1:0.5 to 1:5, preferably 1:0.5, 1:1, 1:2, 1:3, 1:4, 1:5, 1:6, 1:7 or 1:8. In the present application, when forming a pharmaceutically acceptable salt, the free base and the acidic radical are in a molar weight ratio of about 1:0.5 to 1:5, preferably 1:0.5, 1:1, 1:2, 1:3, 1:4, 1:5, 1:6, 1:7 or 1:8.

The term "fixed combination" refers to administration of the active components (for example, the anti-PD-1 antibody or the compound of formula I) to a subject simultaneously at a fixed total dose or in a fixed dose proportion, or in the form of a single substance, pharmaceutical composition or formulation.

The term "non-fixed combination" refers to simultaneous, parallel, or sequential and temporally unlimited administration of two or more aforementioned active components as independent substances (for example, a pharmaceutical composition and a formulation) to a subject, wherein the active components administered to the subject reach therapeutically effective amounts. An example, which can be enumerated, of the non-fixed combination is a cocktail therapy, for example, 3 or more active components are administered. In a non-fixed combination, each active component can be packaged, sold or administered as a fully independent pharmaceutical composition. The term "non-fixed combination" also includes combined use of "fixed combinations", or a "fixed combination" and an independent substance of any one or more active components.

As used herein, "combined use" or "use in combination" means that two or more active substances may be administered to a subject as a mixture, simultaneously as a single formulation, or sequentially in any order as a single formulation.

The term "pharmaceutical composition" refers to a mixture consisting of one or more of the active ingredients (e.g., anti-PD-1 antibody or the compound of formula I) or the therapeutic combinations thereof disclosed herein and a pharmaceutically acceptable excipient. The pharmaceutical composition is intended to facilitate the administration of the compound or the therapeutic combination thereof to a subject.

The term "synergistic effect" means that the effect (e.g., inhibiting the growth of colon cancer or alleviating the symptoms of colon cancer) generated by two or more ingredients (e.g., anti-PD-1 antibody or the compound of formula I) is superior to the simple addition of effects of separately administering the ingredients.

Manner of Administration

The content below is not intended to limit the manner of administration of the therapeutic combination disclosed herein.

The components in the therapeutic combination disclosed herein can be formulated separately, or some or all of the active components are co-formulated. In one embodiment, the therapeutic combination disclosed herein can be formulated into a pharmaceutical composition which is suitable for a single dose or multiple doses.

The components in the therapeutic combination disclosed herein can be administered separately, or some or all of the components are co-administered. The components in the therapeutic combination disclosed herein can be administered in a substantially asynchronous manner, or some or all of the components are administered in a substantially synchronous manner.

The components in the therapeutic combination disclosed herein can be administered independently, or some or all of the components are co-administered in various proper routes, including, but not limited to, oral administration or parenteral administration (by intravenous, intramuscular, local or subcutaneous routes). In some embodiments, the components in the therapeutic combination disclosed herein can be administered independently, or some or all of the components are co-administered by means of oral administration or injection, for example, intravenous injection or intraperitoneal injection.

The components in the therapeutic combination disclosed herein can be independent suitable dosage forms, or some or all of the components are co-formulated in a suitable dosage form including, but not limited to, tablet, lozenge, pill, capsule (for example, hard capsule, soft capsule, enteric capsule and microcapsule), elixir, granule, syrup, injection (intramuscular, intravenous and intraperitoneal), granule, emulsion, suspension, solution, dispersant and dosage forms of slow-released preparations for oral or non-oral administration.

The components in the therapeutic combination disclosed herein can be formulated independently, or some or all of the components are co-formulated with a pharmaceutically acceptable carrier and/or excipient.

The therapeutic combination may further comprise an additional therapeutic agent. In one embodiment, the additional therapeutic agent can be a known cancer therapeutic agent in the art, preferably a lung cancer therapeutic agent.

In some specific embodiments, the present application studies the therapeutic effects on lung tumor of single use or combined use of anlotinib hydrochloride and an anti-PD-1 antibody. Surprisingly, the experimental results show that the anlotinib hydrochloride and the anti-PD-1 antibody can have obvious synergistic effect which breaks the immune tolerance to the tumor cells established by the body.

DETAILED DESCRIPTION

Figure 1:
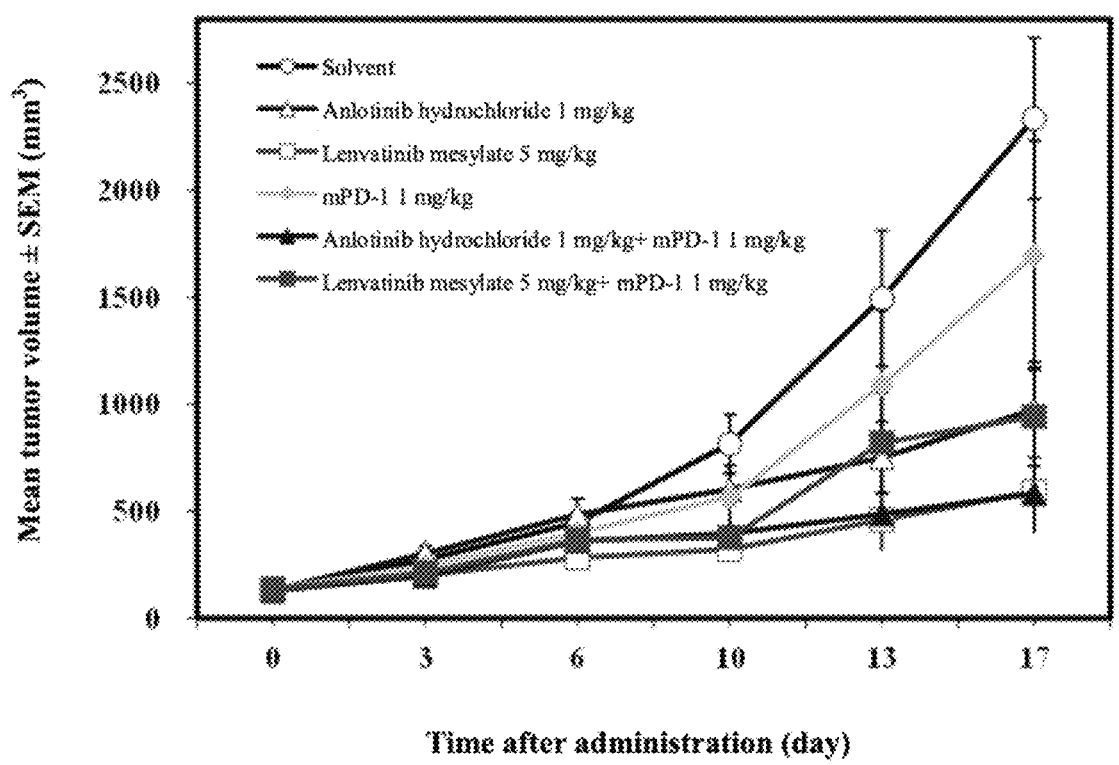
FIG. 1 shows the effects of single use of anlotinib hydrochloride and lenvatinib mesylate and their respective combined use with anti-mPD-1 antibody on the growth of mouse liver cancer H22 subcutaneous xenograft tumor.

The present application is further described below with reference to specific examples, which are, however, only for illustration and do not limit the scope of the present application. Likewise, the present application is not limited to any particular preferred embodiment described herein. It should be understood by those skilled in the art that equivalent substitutions and corresponding modifications of the technical features of the present application still fall within the protective scope of the present application. Unless otherwise specified, the reagents used in the following examples are commercially available products, and the solutions can be prepared by conventional techniques in the art.

TABLE 1

List of abbreviations

| Abbreviation | Explanation |
|---|---|
| ADA | Anti-drug antibody |
| ADCC | Antibody-dependent cell-mediated cytotoxicity |
| AE | Adverse event |
| AKT | Protein kinase B |
| ALB | Albumin |
| ALP | Alkaline phosphatase |
| ALT | Alanine aminotransferase |
| ANA | Antinuclear antibody |
| ANC | Absolute neutrophil count |
| APTT | Activated partial thromboplastin time |
| ASCT | Autologous hematopoietic stem cell transplantation |
| AST | Aspartate aminotransferase |
| BSA | Body surface area |
| CAR-T | Chimeric antigen receptor T-cell immunotherapy |
| CI | Confidence interval |
| CK | Creatine kinase |
| CK-MB | Creatine kinase-MB |
| CL | Clearance |
| Cmax | Peak concentration, maximum blood concentration |
| Cmin | Trough concentration |
| CNS | Central nervous system |
| CPS | Combined positive score, the number of PD-L1 staining cells (tumor cells and immune cells) divided by the total number of viable tumor cells |
| Cr | Creatinine |
| CR | Complete response |
| CRA | Clinical research associate |
| CRO | Contract research organization |
| CT | Computed tomography |
| CTCAE | Common terminology criteria for adverse events |
| CTLA-4 | Cytotoxic T lymphocyte associated antigen 4 |
| CSS | Steady-state concentration |
| DBIL | Direct bilirubin |
| DCR | Disease control rate |
| DNA | Deoxyribonucleic acid |
| DOR | Duration of response |
| DC cell | Dendritic cell |
| D-Dimer | D dimer |
| EC50 | Half maximal effect concentration |
| ECOG | Eastern Cooperative Oncology Group |
| EC | Ethics committee |
| ECG | Electrocardiogram |
| eCRF | Electronic case report form |
| EDC | Electronic data capture |
| EPO | Erythropoietin |
| EMA | European Medicines Agency |
| FDA | Food and Drug Administration |
| FDG | 18F-deoxyglucose |
| FGB | Fibrinogen |
| GCP | Good clinical practice |
| GGT | Gamma-glutamyltransferase |
| GM-CSF | Granulocyte-macrophage colony stimulating factor |
| Glu | Glucose |
| HDT | High dose chemotherapy |
| HGB | Hemoglobin |
| HIV | Human immunodeficiency virus |
| HPV | Human papilloma virus |
| ICH | International conference on harmonization |
| IEC | Independent ethics committee |
| IFN | Interferon |

TABLE 1-continued

List of abbreviations

| Abbreviation | Explanation |
|---|---|
| Ig | Immunoglobulin |
| IL | Interleukin |
| IHC | Immunohistochemical examination |
| INR | International normalized ratio |
| IRB | Institutional review board |
| IRR | Infusion related reaction |
| ITSM | Immunoreceptor tyrosine switch motif |
| IV | Intravenous |
| Keytruda | Pembrolizumab |
| LDH | Lactate dehydrogenase |
| LVEF | Left ventricular ejection fraction |
| MedDRA | Medical Dictionary for Regulatory Activities |
| NLPHL | Nodular lymphocyte predominance Hodgkin lymphoma |
| NOAEL | No observed adverse effect level |
| MTD | Maximum tolerated dose |
| MRI | Magnetic resonance imaging |
| NCI | National cancer institute |
| NYHA | New York Heart Disease Association |
| ORR | Objective response rate |
| OS | Overall survival |
| Opdivo | Nivolumab injection |
| PD | Progression of disease |
| PD-1 | Programmed death receptor 1 |
| PD-L1 | Programmed death ligand 1 |
| PD-L2 | Programmed death ligand 2 |
| PET-CT | Positron emission tomography-computed tomography |
| PI3K | Phosphatidylinositol 3 kinase |
| PKC | Protein kinase C |
| PKCS | PK concentration set |
| PKPS | PK parameter set |
| Pembrolizu-mab | Pembrolizumab |
| PFS | Progression-free survival |
| PS | Performance status |
| PLT | Platelet |
| PK | Pharmacokinetics |
| p.o. | Per os |
| PT | Prothrombin time |
| PPS | Per protocol set |
| PT | Plasma prothrombin time |
| QTc | Corrected QT interval |
| RBC | Red blood cell |
| RECIST | Response evaluation criteria in solid tumors |
| R/M SCCHN | Recurrent/metastatic Squamous head and neck |
| SAE | Severe adverse event |
| SCCHN | Squamous cell carcinoma of the head and neck |
| SDV | Source data verification |
| SUSAR | Suspected unexpected serious adverse reaction |
| SLE | Systemic lupus erythematosus |
| SS | Safety set |
| SUSAR | Suspected unexpected serious adverse reaction |
| T1 | The tumor has grown into the submucosa |
| T1/2 | Half life |
| Ta | Noninvasive papillary carcinoma |
| TCR | T cell receptor |
| Tecentriq ® | Atezolizumab |
| TEN | Toxic epidermal necrolysis |
| TPS | Tumor proportion score |
| Tis | Carcinoma in situ |
| Tmax | Time to peak |
| TMB | Tumor mutational burden |
| TNF | Tumor necrosis factor |
| ULN | Upper limit of normal |
| Vss | Volume of distribution at steady state |

Example 1: Combination Therapy with Anlotinib Hydrochloride for Treatment of Advanced Non-Small Cell Lung Cancer This example discloses the results of an exploratory study on the combination therapy with anlotinib hydrochloride for the treatment of advanced non-small cell lung cancer. The main target population are patients with locally advanced (IIIB), metastatic or recurrent (stage IV) NSCLC who are driver gene-negative (i.e., EGFR, ALK and ROS1 mutation negative) and histologically or cytologically confirmed to be unsuitable for surgery and unable to receive radical concurrent radiotherapy and chemotherapy.

Primary research endpoints: security and ORR.
Secondary research endpoints: DCR, PFS and OS.
Progression-free survival (PFS): defined as the time from the first dose until objective progression or death of the tumor.

Overall survival (OS): defined as the time from the first dose to death due to any cause. For subjects who are lost to follow-up, the time of the last follow-up is typically regarded as the death time, calculated by days.

Key inclusion criteria: stage IIIB/IV NSCLC in China; has not received systemic treatment; the molecular typing is definite; 18-75 years old; PS score: 0-1; expected life span exceeds 3 months; has sufficient organ reserve function; asymptomatic brain metastasis.

Key exclusion criteria: prior receipt of systemic anti-cancer therapy; has various factors affecting oral drugs; people known to have symptomatic brain metastasis, spinal cord compression, and cancerous meningitis or people found to be have brain diseases or leptomeningeal diseases by CT or MRI examination at screening; has central cavernous squamous carcinoma or bleeding tendency; patients with any severe and/or uncontrolled disease. Anlotinib hydrochloride: pale yellow crystalline powder with a content of 98.9%; batch number: 17316007, stored at 2-8° C. in the absence of light. The anlotinib hydrochloride was provided by Chia Tai Tianqing Pharmaceutical Group Co., Ltd. The anlotinib hydrochloride was prepared with distilled water and diluted to the required concentration.

Administration Dose:

Anti-PD-1 antibody: on the first day (D1) of each cycle (21 days in total), 200 mg of sintilimab injection was intravenously infused, once every 21 days.

Anlotinib hydrochloride capsule (its active ingredient was anlotinib dihydrochloride): 5 minutes before or after the start of the infusion of the anti-PD-1 antibody injection, 12 mg of anlotinib hydrochloride capsule was given orally on an empty stomach, and the oral administration continued for 2 weeks and interrupted for 1 week, namely a treatment cycle of 21 days.

Before the trial began, the trial protocol, the copy of the electronic case report form, the sample of the informed consent form and the like of the trial were submitted to ethical committees of the institution responsible for the clinical research and other institutions involved in the research for review, and the clinical trial could be carried out only after acquiring the approval of the ethical committees. Before the clinical trial began, researchers gave detailed description of the purpose, risk and benefit of the trial to all subjects to ensure that all the subjects were informed and signed the informed consent before the trial, and fully guarantee the rights and interests of the subjects during the trial. Investigators strictly comply with ethical principles for medical research involving human subjects in Declaration of Helsinki (2013) and stipulations of relevant laws and regulations like Good Clinical Practice (2003) while performing their duties.

Eleven patients were qualified for efficacy evaluation by Jan. 25, 2019. The basic status and efficacy evaluation results of the 11 patients enrolled in the research are shown in Table 2, wherein the efficacy evaluation were carried out at the second cycle (about 42 days) and the fourth cycle (about 84 days); and the statistical results of the efficacy evaluations are presented in Table 3.

TABLE 2

Basic status and efficacy evaluation results of patients enrolled in the research

| Number | Age | Pathology | Staging | Time of first administration | Efficacy evaluation Second cycle | Efficacy evaluation Fourth cycle |
|---|---|---|---|---|---|---|
| 1 | 71 | Adenocarcinoma | C-T2N1M1a (brain) stage IV | 2018 Sep. 21 | SD (−25.32%) | PR (−42.8%) |
| 2 | 64 | Squamous carcinoma | C-T4N3M0 stage IIIb | 2018 Oct. 17 | SD (−6.65%) | SD (−18.92%) |
| 3 | 66 | Squamous carcinoma | C-T2bN3M0 stage IIIb | 2018 Nov. 1 | PR (−33.02%) | PR (−53.11%) |
| 4 | 61 | Adenocarcinoma | C-T4 (invasion of chest wall) stage IIIc | 2018 Nov. 5 | PR (−50.63%) | |
| 5 | 65 | NSCLC | C-T2bN3M0 stage IIIb | 2018 Nov. 12 | PR (−31.11%) | |
| 6 | 58 | Squamous carcinoma | C-T1N3 (supraclavicular) stage M0 IIIb | 2018 Nov. 20 | PR (−21.0%) | |
| 7 | 65 | Adenocarcinoma | C-T1aN3M0 stage IV | 2018 Nov. 30 | SD (−21.05%) | PR (−31.64%) |
| 8 | 65 | Squamous carcinoma | C-T4N3M1 (pleural, intrapulmonary) stage IV | 2018 Dec. 3 | SD (−21.0%) | |
| 9 | 61 | Squamous carcinoma | C-T4N3M0 stage IIIc | 2018 Dec. 6 | SD (−6.59%) | |
| 10 | 61 | Squamous carcinoma | C-T4N3M0 stage IIIb | 2018 Dec. 6 | PR (−30.27%) | |
| 11 | 68 | Squamous carcinoma | C-T2N2M1 (bone, lung) stage IV | 2018 Dec. 25 | SD (−27.76%) | |

The results of the exploratory research on the first-line treatment of advanced non-small cell lung cancer by a combination therapy with anlotinib suggest a surprising efficacy, wherein, when used in combination with sintilimab, the ORR was 63.6%, the DCR was 100% (see Table 3), and PFS and OS were also something to look forward to. At the same time, the first-line combination modality with anlotinib may show a high degree of patient tolerance (detailed results not shown).

TABLE 3

Efficacy evaluation of combined use of anlotinib and sintilimab

| Efficacy | Cases (efficacy evaluation of 11 cases at present) |
|---|---|
| CR | 0/11 (0.0%) |
| PR | 7/11 (63.6%) |
| SD | 4/11 (36.4%) |
| PD | 0/11 (0.0%) |
| ORR | 7/11 (63.6%) |
| DCR | 11/11 (100.0%) |

Example 2: Combination Therapy with Anlotinib Hydrochloride for Treatment of Liver Cancer 1. Drug Information Anlotinib hydrochloride: pale yellow crystalline powder with a content of 98.9%; batch number: 17316007; expiration date: December 2018; stored at 2-8° C. in the absence of light.

Lenvatinib mesylate: off-white crystalline powder with a content of 98.7%; batch number: 19916003; expiration date: June 2019; stored at 2-8° C. in the absence of light.

Anti-mouse PD-1 (abbreviation: mPD-1): colorless transparent liquid with purity of 95% and concentration of 7.83 mg/mL; batch number: 665418F1; stored at 2-8° C. in the absence of light.

2. Suppliers

Anlotinib hydrochloride and lenvatinib mesylate were provided by Chia Tai Tianqing Pharmaceutical Group Co., Ltd.

mPD-1 was purchased from Bio X Cell (specifications: InVivoMAb anti-mouse PD-1 (CD 279)).

3. Preparation Method

The anlotinib hydrochloride and lenvatinib mesylate were prepared with distilled water and diluted to the required concentrations; mPD-1 was diluted with physiological saline to the required concentration and prepared when needed.

4. Cells

The H22 cells were cultured in a 10-cm petri dish with RPMI 1640 medium containing 10% fetal bovine serum, penicillin and streptomycin in an incubator at 37° C. and 5% $CO_2$. Subculturing was carried out twice a week and cells were collected, counted and inoculated when the cells grew exponentially.

5. Laboratory Animals

KM mice, 6-7 weeks old, female, purchased from Shanghai JSJ Laboratory Animal Co. Ltd. Production license No.: SCXK (Shanghai) 2013-0006; animal certification No.: 311620400013790. Breeding environment: SPF grade.

The use and welfare of the laboratory animals were carried out in compliance with the provisions of Association for Assessment and Accreditation of Laboratory Animal Care, International (AAALAC). The health and death of the animals are monitored daily and routine examinations include observation of the effects of the test substance or drug on the daily performance of the animals, such as behavioral activities, weight changes, appearance, etc.

6. Experimental Index

The experimental index is to study the influence of the drug on the tumor growth, and the specific index is T/C (%) or tumor growth inhibition TGI (%).

Tumor diameters were measured twice weekly with a vernier caliper and tumor volume (V) was calculated according to the following formula:

$V = 1/2 \times a \times b^2$, where $a$ and $b$ represent length and width, respectively.

T/C (%)=$(T-T_0)/(C-C_0) \times 100$, where T and C are the tumor volumes of animals at the end of the experiment in the test group and control group, respectively; $T_0$ and $C_0$ are the tumor volumes of animals at the beginning of the experiment in the test group and control group, respectively.

Tumor growth inhibition (TGI)(%)=100−T/C(%).

Tumor growth inhibition (TGI)(%)=100−$(T-T_0)/T_0 \times$ 100 when tumor started to regress.

If the volume of tumor shrinks compared with its initial volume, i.e., $T<T_0$ or $C<C_0$, it is defined as partial regression (PR) of tumor; if the tumor completely disappears, it is defined as complete regression (CR) of tumor.

7. Implementation of Experiment

H22 cells were inoculated to each mouse subcutaneously, and when the tumor grew to 100-200 mm³, the mice were randomly grouped and intragastrically (i.g.) administered or intraperitoneal (IP) injected with drug; the mice in the solvent group were intragastrically administrated with distilled water with the same volume; the administration volume was 0.1 mL/10 g body weight; specific administration dosages and regimes are shown in Table 4.

TABLE 4

Administration dose and regimes

| Tumor | Drug | Animal # | Dose (mg/kg) | Route of administration | Time of administration |
|---|---|---|---|---|---|
| H22 | Control | 10 | Solvent | i.g. | QD × 17 |
| | Anlotinib hydrochloride | 10 | 1 | i.g. | QD × 17 |
| | Lenvatinib mesylate | 10 | 5 | i.g. | QD × 17 |
| | mPD-1 | 10 | 1 | IP | D0, D3, D7, D10, D14 |
| | Anlotinib hydrochloride + mPD-1 | 10 | 1/1 | i.g./IP | QD × 17/D0, D3, D7, D10, D14 |
| | Lenvatinib mesylate + mPD-1 | 10 | 5/1 | i.g./IP | QD × 17/D0, D3, D7, D10, D14 |

Note:
randomly grouped, the time of first administration was $D_0$;
IP: intraperitoneal injection;
i.g.: intragastric administration;
QD: once daily.

After the experiment was completed, or when the tumor volume of the animals reached the euthanization endpoint of 1500 mm$^3$, the animals were put to death through carbon dioxide inhalation, followed by dissecting to take the tumor tissue and weighing and photographing.

8. Experiment Results

Anlotinib hydrochloride (1 mg/kg, i.g., QD×17) can inhibit the growth of the liver cancer H22 subcutaneous xenograft tumor in mice and the TGI is 61.7%; the TGI of lenvatinib mesylate (5 mg/kg, i.g., QD×17) for H22 subcutaneous xenograft tumor is 79%; mPD-1 (1 mg/kg, IP, twice weekly, 5 times in total) has 29.3% TGI for H22, with complete tumor regression in 2/10 mice; the combined use of the anlotinib hydrochloride and the mPD-1 can improve the TGI to 79.5%, with partial regression of tumor in 1/10 mice and complete regression in 1/10 mice; the combined use of lenvatinib mesylate and mPD-1 shows 63.4% TGI for H22, with partial regression of tumor in 1/10 mice. The tumor-bearing mice could well tolerate the combined use of anlotinib hydrochloride and mPD-1 and no obvious symptom such as weight loss was observed. Compared with the efficacy of single use of anlotinib hydrochloride or the mPD-1 on the liver cancer H22 subcutaneous xenograft tumor, the efficacy of the combined use of the anlotinib hydrochloride and the mPD-1 is stronger. The results are shown in Table 5.

shows a rapid growth trend, and the growth of the anlotinib hydrochloride (1 mg/kg)+mPD-1 (1 mg/kg) group is the most gradual.

Figure 3:
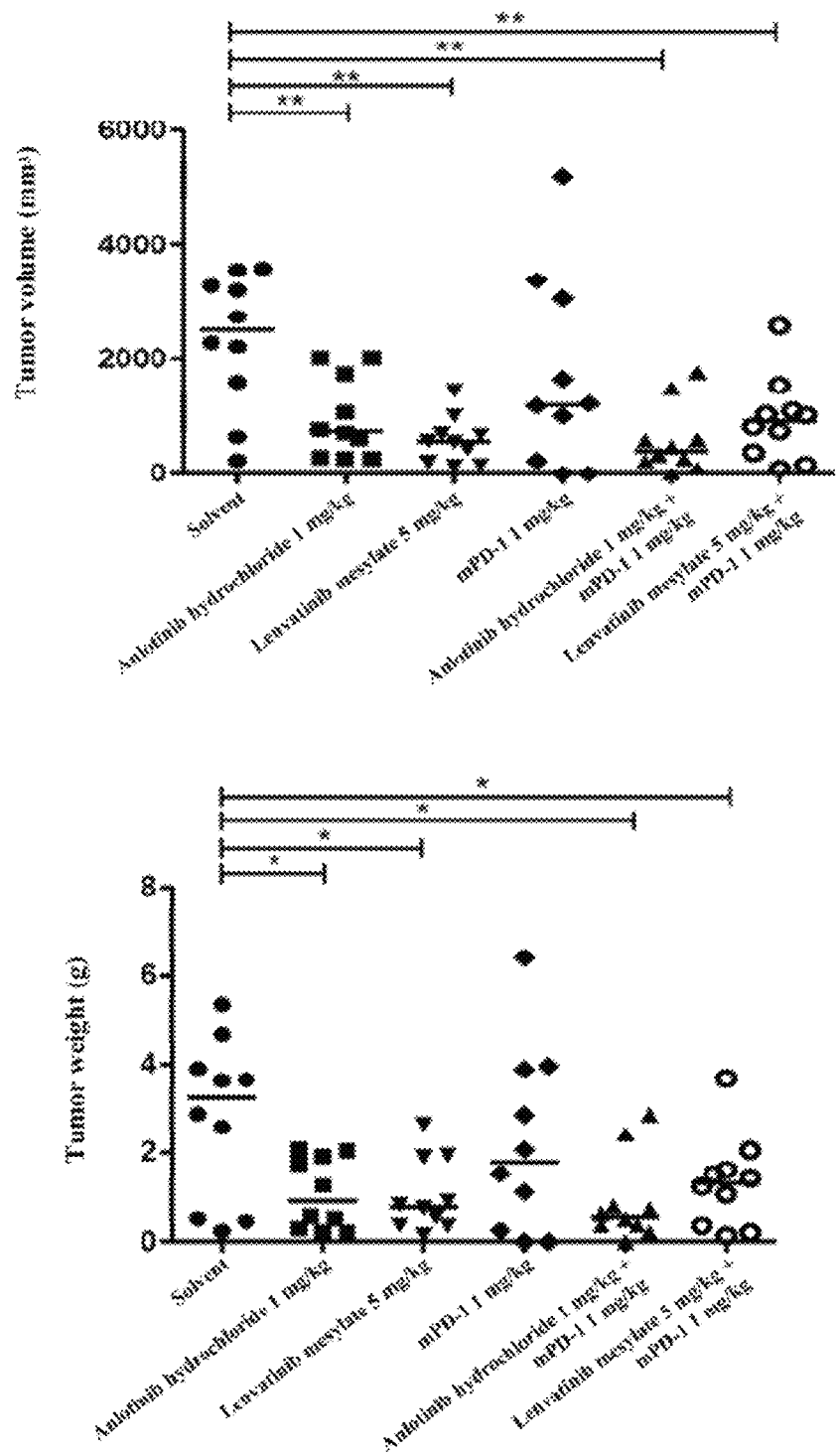
FIG. 3 shows individual tumor volumes (figure above) and individual tumor weights (figure below) at the end of the experiment (D17) for treatment groups of single use of anlotinib hydrochloride and lenvatinib mesylate or their respective combined use with anti-mPD-1 antibody.

FIG. 3 shows the individual tumor volumes and tumor weights of mice in each dose group at the end of the experiment (D17): solvent control group>mPD-1 (1 mg/kg) group>lenvatinib mesylate (5 mg/kg) group+mPD-1 (1 mg/kg) group>anlotinib hydrochloride (1 mg/kg) group>lenvatinib mesylate (5 mg/kg) group>anlotinib hydrochloride (1 mg/kg) group+mPD-1 (1 mg/kg) group.

Figure 4:
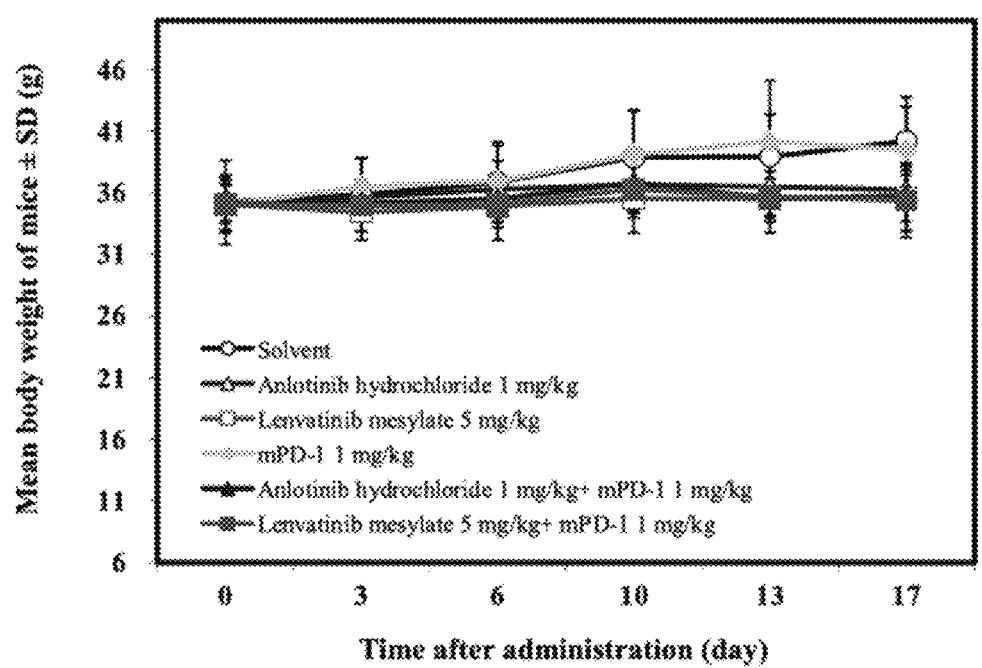
FIG. 4 shows the effects of single use of anlotinib hydrochloride and lenvatinib mesylate or their respective combined use with anti-mPD-1 antibody on body weight of tumor-bearing mice.

As shown in FIG. 4, during D0-D17 after drug administration, the mice in solvent control group and mPD-1 group show a steady increase in body weight, and no symptom like obvious weight loss is found in the groups of lenvatinib mesylate (5 mg/kg)+mPD-1 (1 mg/kg), anlotinib hydrochloride (1 mg/kg), lenvatinib mesylate (5 mg/kg), and anlotinib hydrochloride (1 mg/kg)+mPD-1 (1 mg/kg).

Figure 5:
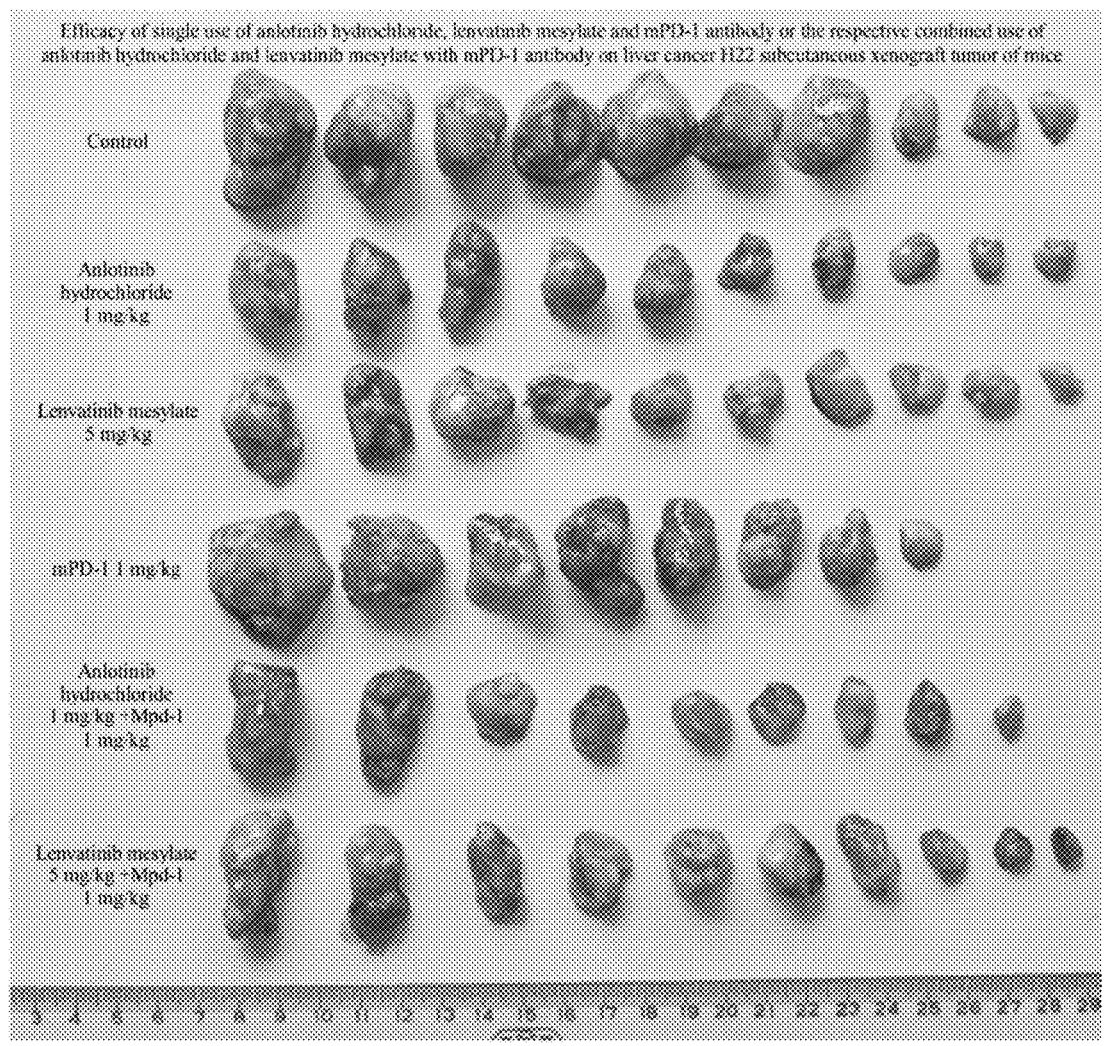
FIG. 5 is a picture of tumors showing the efficacy of single use of anlotinib hydrochloride and lenvatinib mesylate or their respective combined use with anti-mPD-1 antibody on liver cancer H22 subcutaneous xenograft tumor.

As shown in FIG. 5, after the end of administration, the mice were dissected to take the tumors, and the tumor growth was found to be consistent with the results shown in FIG. 1.

The lenvatinib mesylate (5 mg/kg, i.g., QD □ 17) obviously inhibits the growth of mouse liver cancer H22 subcutaneous xenograft tumor, and the anlotinib hydrochloride (1 mg/kg)+mPD-1 (1 mg/kg) can achieve basically the same tumor inhibition effect, and its effect in inhibiting the tumor

TABLE 5

Efficacy on mouse liver cancer H22 subcutaneous xenograft tumor

| | Item | | | | | | | | |
|---|---|---|---|---|---|---|---|---|---|
| | Mean tumor volume (mm$^3$) | | Mean tumor volume (mm$^3$) | | % T/C | Tumor growth inhibition | Partial regression | Complete regression | Beginning of experiment Number of animals per group | End of experiment Number of animals per group |
| | D0 | SEM | D17 | SEM | D17 | (%) | | | | |
| Solvent | 130.1 | ±5.7 | 2336.1 | ±376.4 | — | — | 0 | 0 | 10 | 10 |
| Anlotinib hydrochloride 1 mg/kg | 131.4 | ±4.7 | 975.3 | ±224.9 | 38.3 | 61.7 | 0 | 0 | 10 | 10 |
| Lenvatinib mesylate 5 mg/kg | 127.6 | ±4.0 | 590.8 | ±129.5 | 21.0 | 79.0 | 0 | 0 | 10 | 10 |
| mPD-1 1 mg/kg | 135.9 | ±4.6 | 1696.1 | ±536.1 | 70.7 | 29.3 | 0 | 2 | 10 | 10 |
| Anlotinib hydrochloride 1 mg/kg + mPD-1 1 mg/kg | 131.3 | ±3.0 | 583.9 | ±185.8 | 20.5 | 79.5 | 1 | 1 | 10 | 10 |
| Lenvatinib mesylate 5 mg/kg + mPD-1 1 mg/kg | 135.9 | ±6.4 | 942.4 | ±230.5 | 36.6 | 63.4 | 1 | 0 | 10 | 10 |

The tumor status of mice in each administration group was analyzed, and the results are shown below.

As shown in FIG. 1, from D0 to D17, the mean tumor volume of mice in each group increased with elapsing of administration days, but the increment was different in each group. The mean tumor volume increases most rapidly in the mice of the solvent control group, with the largest volume observed at D17, and the D17 mean tumor volumes of other groups are as follows: mPD-1 (1 mg/kg)>anlotinib hydrochloride (1 mg/kg)>lenvatinib mesylate (5 mg/kg)+mPD-1 (1 mg/kg)>anlotinib hydrochloride (1 mg/kg)+mPD-1 (1 mg/kg)>lenvatinib mesylate (5 mg/kg).

Figure 2:
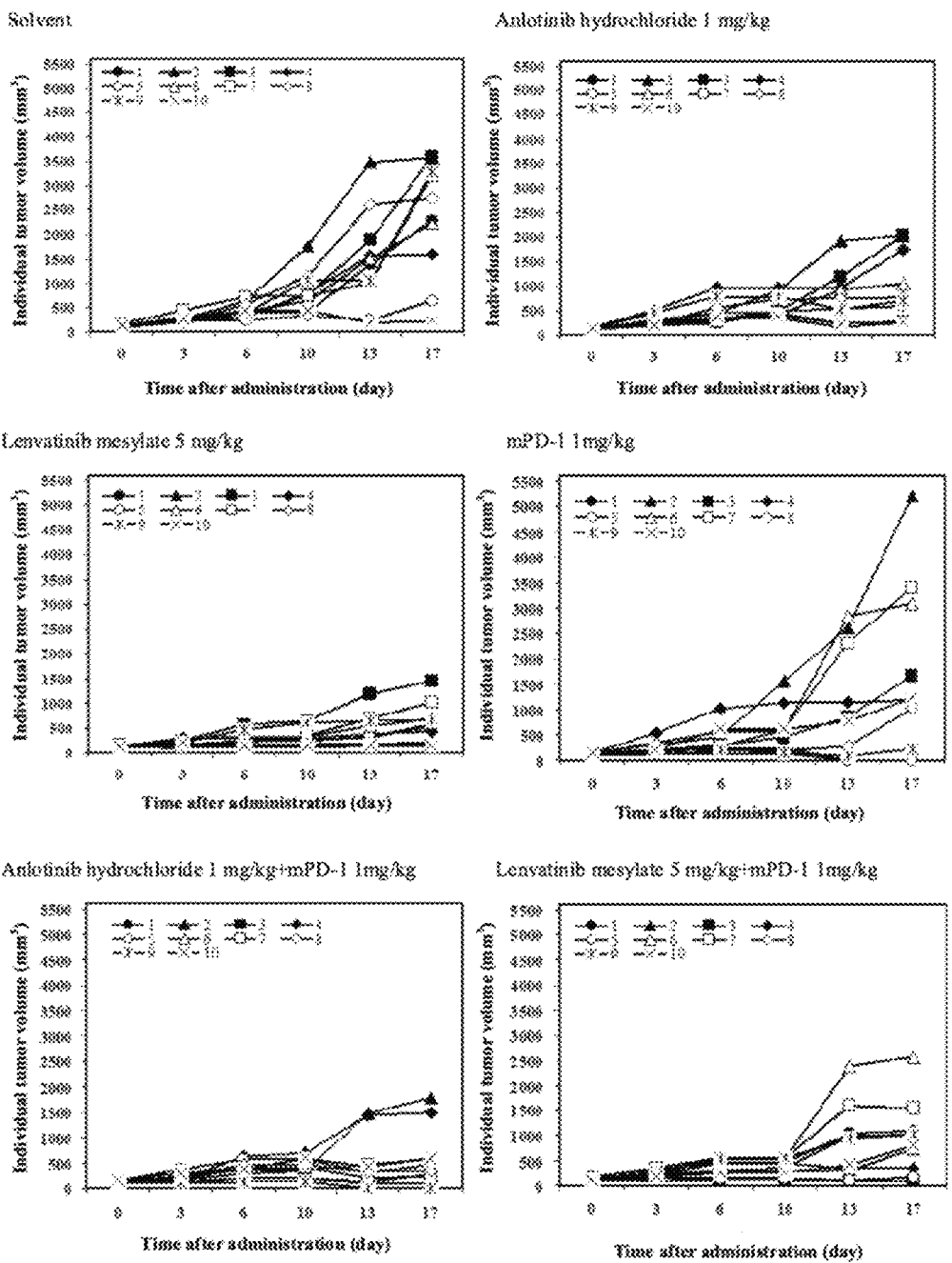
FIG. 2 shows individual tumor growth curves of mice in treatment groups of single use of anlotinib hydrochloride and lenvatinib mesylate or their respective combined use with anti-mPD-1 antibody.

As shown in FIG. 2, during D0-D17 after drug administration, the tumor growth in mice of each group is more consistent with that of FIG. 1, the solvent control group growth is superior to that of the lenvatinib mesylate while its dose can be greatly reduced, which is beneficial to reducing side effect of the drug; the mPD-1 has a certain efficacy on H22, but the combined use of the anlotinib hydrochloride and the mPD-1 can obviously improve the tumor growth inhibition for H22, and the tumor-bearing mice can well tolerate the combined use of the two drugs.

Example 3: Preparation of Anti-PD-1 Monoclonal Antibody

Establishment of PD-1 Hybridoma Cell Strain

1. Fusion protein PD-1 with corresponding amino acid sequence was prepared according to molecular biological method, and the PD-1 fusion protein prepared by the above-mentioned method was used as an antigen and emulsified with Freund's adjuvant to immunize BALB/C mouse. After the immune response was produced in mice, spleen cells were taken out and fused with mouse myeloma cells to form hybridoma cells, and the resulting hybridoma cells were cultured using a 96-well plate.

2. For the antibody secreted by each hybridoma cell strain, PD-1-hFc was used as antigen to coat the microplate, 1% BSA-containing PBS buffer solution was used for sealing the microplate, and the coated microplate was used for screening, by an indirect ELISA method, the hybridoma cells secreting a new antibody which specifically binds to PD-1.

3. Hybridoma cells that are capable of secreting a monoclonal antibody that competes with PD-L1 for binding to PD-1 were screened, by a competitive ELISA method, from hybridoma cells acquired by indirect ELISA screening.

4. The cell strain acquired by screening was subcloned to get a monoclonal stable cell strain secreting the antibody which competes with PD-L1 for specifically binding to PD-1. Specific method is as follows: living cell count was performed for the cells to be subcloned, which were then diluted with IMDM medium containing 15% fetal bovine serum according to the number of the living cells and inoculated into a 96-well cell culture plate for culturing, wherein the theoretical cell density of the inoculation is 1 cell/well; after growing into a monoclonal cell mass, the cells were screened by an ELISA method, and a stable monoclonal cell strain was acquired after multiple times of subcloning and screening.

5. After acquiring the stable cell strain, the stable cell strain was cultured in medium containing 10% low IgG fetal bovine serum, and after 7-10 days of culturing, cell supernatant was collected for antibody purification so as to get the corresponding anti-PD-1 antibody.

Humanization Design of Antibody

To construct a humanized antibody, the variable region amino acid sequence of a murine antibody is aligned with the human variable region gene sequence. Through selective mutation of partial murine amino acid sequence to humanized amino acid sequence, a variety of humanized antibodies are designed.

The heavy chain variable region sequence of humanized antibody 1 is:

```
                                                 (SEQ ID NO: 1)
EVKLVESGGGLVKPGGSLKLSCAASGFTFSSYGMSWVRQTPEKSLEWVATI

SGGGSDTYYPD SVKGRFTISRDNAKNNLYLQMSSLRSEDTALYYCARQLN

YAWFAYWGQGTLVTVSAAKTTPPSVYRSSKGNSSTLAAVTS
```

The light chain variable region sequence of humanized antibody 1 is:

```
                                                 (SEQ ID NO: 4)
DIVLTQSPASLAVSLGQRATISCRASESVDNYGISFMNWFQQKPGQPPKLL

IYTSSNQGSGVPARFSGSGSGTDFSLNIHPMEEDDTAMYFCQQSKEVPWTF

GGGTKLEIKR
```

The heavy chain variable region sequence of humanized antibody 2 is:

```
                                                 (SEQ ID NO: 2)
EVQLVESGGGLVQPGGSLRLSCAASGFTFSSYGMSWVRQAPGKGLEWVATI

SGGGSDTYYPDSVKGRFTISRDNSKNNLYLQMSSLRAEDTAVYYCARQLNY

AWFAYWGQGTLVTVSS
```

The light chain variable region sequence of humanized antibody 2 is:

```
                                                 (SEQ ID NO: 5)
DIVLTQSPASLAVSPGQRATITCRASESVDNYGISFMNWFQQKPGQPPKLL

IYTSSNQGTGVPARFSGSGSGTDFTLNINPMEADDTAMYFCQQSKEVPWTF

GGGTKLEIK
```

The heavy chain variable region sequence of humanized antibody 3 is:

```
                                                 (SEQ ID NO: 3)
EVQLVESGGGLVQPGGSLRLSCAASGFTFSSYGMSWVRQAPGKGLEWVATI

SGGGSDTYYADSVKGRFTISRDNSKNTLYLQMNSLRAEDTAVYYCARQLNY

AWFAYWGQGTLVTVSS
```

The light chain variable region sequence of humanized antibody 3 is:

```
                                                 (SEQ ID NO: 6)
DIVLTQSPASLAVSPGQRATITCRASESVDNYGISFMNWYQQKPGQPPKLL

IYTSSNKDTGVPARFSGSGSGTDFTLTINPMEAEDTAVYYCQQSKEVPWTF

GGGTKLEIK
```

The heavy chain variable region sequence of humanized antibody 4 is:

```
                                                 (SEQ ID NO: 7)
EVKLVESGGGLVKPGGSLKLSCAASGFAFSSYDMSWVRQTPEKRLEWVATI

SGGGRYTYYPDSVKGRFTISRDNARNTLYLQMSSLRSEDTALYYCANRYGE

AWFAYWGQGTLVTVSA
```

The light chain variable region sequence of humanized antibody 4 is:

```
                                                 (SEQ ID NO: 9)
DIKMTQSPSSMYASLGERVTFTCKASQDINTYLSWFQQKPGKSPKTLIYRA

NRLVDGVPSRFSGSGSGQDYSLTISSLEYEDMGIYYCLQYDEFPLTFGAGT

KLEL
```

The heavy chain variable region sequence of humanized antibody 5 is:

```
                                                 (SEQ ID NO: 8)
EVQLVESGGGLVQPGGSLRLSCAASGFAFSSYDMSWVRQAPGKGLDWVATI

SGGGRYTYYPDSVKGRFTISRDNSKNNLYLQMNSLRAEDTALYYCANRYGE

AWFAYWGQGTLVTVSS
```

The light chain variable region sequence of humanized antibody 5 is:

```
                                                 (SEQ ID NO: 10)
DIQMTQSPSSMSASVGDRVTFTCRASQDINTYLSWFQQKPGKSPKTLIYRA

NRLVSGVPSRFSGSGSGQDYTLTISSLQPEDMATYYCLQYDEFPLTFGAGT

KLELK
```

The heavy chain variable region sequence of humanized antibody 6 is:

(SEQ ID NO: 11)
EVQLVQSGGGLVQPGGSLKLSCAASGFTFSSYGMSWVRQTPEKGLDWVATI
SGGGRDTYYPDSVKGRFTISRDNSKNNLYLQMNSLRAEDTALYYCARQKGE
AWFAYW GQGTLVTVSS

The light chain variable region sequence of humanized antibody 6 is:

(SEQ ID NO: 14)
DIVLTQSPASLAVSPGQRATITCRASESVDNYGISFMNWFQQKPGQPPKLL
IYAASNKGTGVPARFSGSGSGTDFTLNIHPMEENDTAMYFCQQSKEVPWTF
GGGTKLEIK

The heavy chain variable region sequence of humanized antibody 7 is:

(SEQ ID NO: 12)
EVQLVQSGGGLVQPGGSLKLSCAASGFTFSSYGMSWVRQAPGKGLDWVATI
SGGGRDTYYPDSVKGRFTISRDNSKNNLYLQMNSLRAEDTALYYCARQKGE
AWFAYWGQGTLVTVSS

The light chain variable region sequence of humanized antibody 7 is:

(SEQ ID NO: 15)
DIVLTQSPASLAVSPGQRATITCRASESVDNYGISFMNWFQQKPGQPPKLL
IYAASNKGTGVPARFSGSGSGTDFTLNINPMEENDTAMYFCQQSKEVPWTF
GGGTKLEIK

The heavy chain variable region sequence of humanized antibody 8 is:

(SEQ ID NO: 13)
EVQLVQSGGGLVQPGGSLKLSCAASGFTFSSYGMSWVRQAPGKGLDWVATI
SGGGRDTYYPDSVKGRFTISRDNSKNTLYLQMNSLRAEDTAVYYCARQKGE
AWFAYWGQGTLVTVSS

The light chain variable region sequence of humanized antibody 8 is:

(SEQ ID NO: 16)
DIVLTQSPASLAVSPGQRATITCRASESVDNYGISFMNWYQQKPGQPPKL
LIYAASNKATGVPARFSGSGSGTDFTLNINPMEANDTAVYFCQQSKEVPW
TFGGGTKLEIK

The heavy chain sequence of humanized antibody 8A is:

(SEQ ID NO: 17)
EVQLVQSGGGLVQPGGSLKLSCAASGFTFSSYGMSWVRQAPGKGLDWVAT
ISGGGRDTYYPDSVKGRFTISRDNSKNNLYLQMNSLRAEDTALYYCARQK
GEAWFAYWGQGTLVTVSSASTKGPSVFPLAPCSRSTSESTAALGCLVKDY
FPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLM
IRTPEVTCVVVDVSQEDPEVQFNWYVDGVEVHNAKTKPREEQFNSTYRVV
SVLTLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSF
FLYSRLTVDKSRWQEGNVFSCSVMHEALHHYTQKSLSLSLGK

The light chain sequence of humanized antibody 8A is:

(SEQ ID NO: 18)
DIVLTQSPASLAVSPGQRATITCRASESVDNYGISFMNWFQQKPGQPPKL
LIYAASNKGTGVPARFSGSGSGTDFTLNINPMEENDTAMYFCQQSKEVPW
TFGGGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC

The heavy chain variable region sequence of humanized antibody 9 is:

(SEQ ID NO: 31)
QVQLVQSGVEVKKPGASVKVSCKASGYTFTNYYMYWVRQAPGQGLEWMGG
TNPSNGGTNFNEKFKNRVTLTTDSSTTTAYMELKSLQFDDTAVYYCARRD
YRFDMGFDYWGQGTTVTVSS

The light chain variable region sequence of humanized antibody 9 is:

(SEQ ID NO: 34)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIK

The heavy chain sequence of humanized antibody 9 is:

(SEQ ID NO: 37)
QVQLVQSGVEVKKPGASVKVSCKASGYTFTNYYMYWVRQAPGQGLEWMGG
TNPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK

The light chain sequence of humanized antibody 9 is:

(SEQ ID NO: 40)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The heavy chain variable region sequence of humanized antibody 10 is:

(SEQ ID NO: 32)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSS

The light chain variable region sequence of humanized antibody 10 is:

(SEQ ID NO: 35)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK

The heavy chain sequence of humanized antibody 10 is:

(SEQ ID NO: 38)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

The light chain sequence of humanized antibody 10 is:

(SEQ ID NO: 41)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKIIKVYACEVTHQ

GLSSPVTKSFNRGEC

The heavy chain variable region sequence of humanized antibody 11 is:

(SEQ ID NO: 33)
EVQLLESGGVLVQPGGSLRLSCAASGFTFSNFGMTWVRQAPGKGLEWVSG

ISGGGRDTYFADSVKGRFTISRDNSKNTLYLQMNSLKGEDTAVYYCVKWG

NIYFDYWGQGTLVTVSS

The light chain variable region sequence of humanized antibody 11 is:

(SEQ ID NO: 36)
DIQMTQSPSSLSASVGDSITITCRASLSINIFLNWYQQKPGKAPNLLIYA

ASSLHGGVPSRFSGSGSGTDFTLT1RTLQPEDFATYYCQQSSNTPFTFGP

GTVVDFR

The heavy chain sequence of humanized antibody 11 is:

(SEQ ID NO: 39)
EVQLLESGGVLVQPGGSLRLSCAASGFTFSNFGMTWVRQAPGKGLEWVSG

ISGGGRDTYFADSVKGRFTISRDNSKNTLYLQMNSLKGEDTAVYYCVKWG

NIYFDYWGQGTLVTVSSASTKGPSVFPLAPCSRSTSESTAALGCLVKDYF

PEPVTVSWNSGALTSGVHTFPAVLQSSGLYSLSSVVTVPSSSLGTKTYTC

NVDIIKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

The light chain sequence of humanized antibody 11 is:

(SEQ ID NO: 42)
DIQMTQSPSSLSASVGDSITITCRASLSINIFLNWYQQKPGKAPNLLIYA

ASSLHGGVPSRFSGSGSGTDFTLT1RTLQPEDFATYYCQQSSNTPFTFGP

GTVVDFRRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The nucleic acid sequences encoding the humanized antibodies above were obtained through whole-gene synthesis and constructed into an expression vector. Expression vector DNA was extracted to transfect mammal cells (293 cells). After cell transfection, the antibody is expressed inside the mammalian cells and secreted outside the cells. The expressed antibody was purified through an antibody A affinity chromatography column to obtain the humanized antibody protein. These experimental procedures are all conventional procedures known in the art.

Example 4: Clinical Study on First-Line Treatment of Unresectable Hepatocellular Carcinoma with Combined Use of 14C12H1L1 and Anlotinib Hydrochloride This example discloses the results of an early open, multicenter phase Ib/II clinical study on first-line treatment of unresectable hepatocellular carcinoma with combined use of 14C12H1L1 and anlotinib hydrochloride.

This study is an open, multicenter phase Ib/II clinical study aimed at evaluating the effectiveness, i.e. safety, of 14C12H1L1 in combination with anlotinib in the first line treatment of unresectable hepatocellular carcinoma.

Primary endpoint: objective response rate (ORR) evaluated according to RECISIT v1.1.

Secondary endpoints: (1) disease control rate (DCR), duration of response (DOR), time to response (TTR), progression-free survival (PFS), and treatment past progression (TPP) being evaluated by investigators according to RECISIT v1.1; (2) overall survival (OS); (3) safety evaluation: incidence and severity of AEs, clinically significant abnormal laboratory test results.

Progression-free survival (PFS): defined as the time from the first dose until objective progression or death of the tumor.

Overall survival (OS): defined as the time from the first dose to death due to any cause. For subjects who are lost to follow-up, the time of the last follow-up is typically regarded as the death time, calculated by days.

Duration of response (DOR): defined as the time from being evaluated as CR or PR for the first time to being evaluated as PD or death for the first time.

Time to response (TTR): the time from the first dose of the subject to being evaluated as CR or PR for the first time.

Investigational Drugs

14C12H1L1 injection, 100 mg/10 mL solution; manufacturer: Akeso Tiancheng Guangdong Co., Ltd.; stored at 2-8° C. in the absence of light.

Anlotinib hydrochloride capsules (FOCUS V®), 8 mg/capsule; manufacturer: Chia Tai Tianging Pharmaceutical Group Co., Ltd.; sealed and be away from light.

Administration

Administration Regimen and Dose Selection

14C12H1L1 in combination with anlotinib, wherein the 14C12H1L1: 200 mg, Q3W intravenous injection; anlotinib: taken once a day, 8 mg each time, 14 days of treatment plus 7 days of interruption, i.e., a treatment cycle of 21 days.

Results of Early Study

Therapeutic Effects

Figure 6:
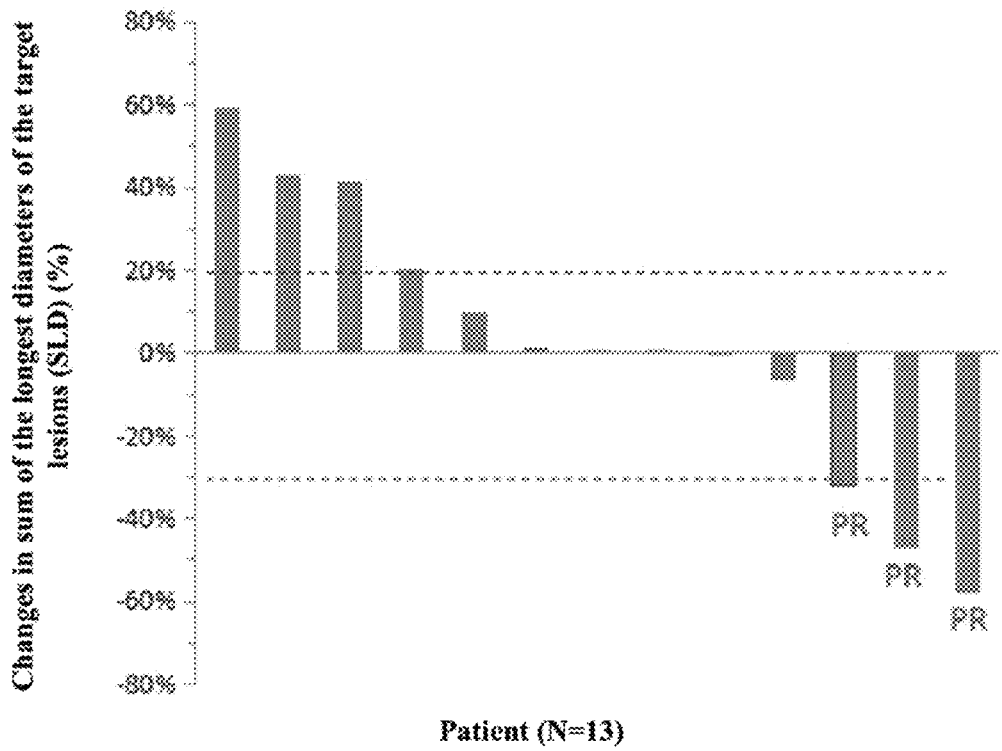
FIG. 6 shows changes in SLD (sum of the longest diameters of the minimum target lesions recorded after the start of treatment) of 13 patients in an open, multicenter Ib/phase II clinical study on first-line treatment of unresectable hepatocellular carcinoma with combined use of 14C12H1L1 and anlotinib hydrochloride.
Figure 7:
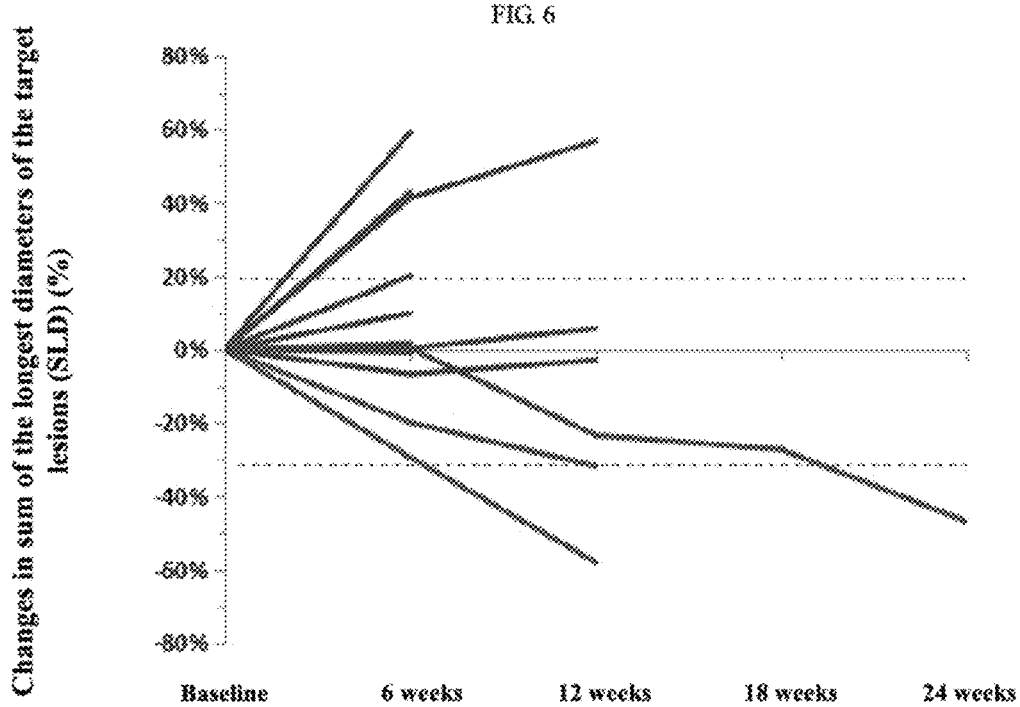
FIG. 7 shows changes in SLD of 13 patients over time in an open, multicenter Ib/phase II clinical study on first-line treatment of unresectable hepatocellular carcinoma with combined use of 14C12H1L1 and anlotinib hydrochloride.

By Jul. 15, 2019, a total of 13 subjects had received at least one tumor assessment with the median treatment cycle being 3. Among these patients, 3 achieved partial response (PR), the objective response rate (ORR) was 23.1% (3/13), and the disease control rate (DCR) was 69.2% (9/13) (FIG. 6, FIG. 7).

Adverse Events

By Jun. 27, 2019, the incidence of treatment-related adverse events (TRAEs) was 75%, with TRAEs of grade 3 and above being 12.5%. The results show that the incidence of adverse events in the first line treatment of unresectable hepatocellular carcinoma with the combined use of 14C12H1L1 and anlotinib hydrochloride (see Table 6) is significantly lower than that of either the single use of anlotinib hydrochloride (data not shown) or the single use of 14C12H1L1 (data not shown).

TABLE 6

Adverse events of the combined use of 14C12H1L1 and anlotinib

| n (%) | Related to all the combined treatments | Related to 14C12H1L1 | Related to Anlotinib |
|---|---|---|---|
| TRAE | 75% | 62.5% | 75% |
| ≥ grade 3 TRAEs | 12.5% | 6.25% | 12.5% |
| SAE | 12.5% | 6.25% | 12.5% |
| TRAEs resulting in the withdrawal | 12.5% | 6.25% | 12.5% |

The exemplary embodiments described herein can be described by the following numbered paragraphs:

1. A therapeutic combination, comprising:
   a) an inhibitor for the interaction between PD-1 and its ligand PD-L1, and
   b) a tyrosine kinase inhibitor, wherein the tyrosine kinase inhibitor is a compound of formula I or a pharmaceutically acceptable salt thereof,

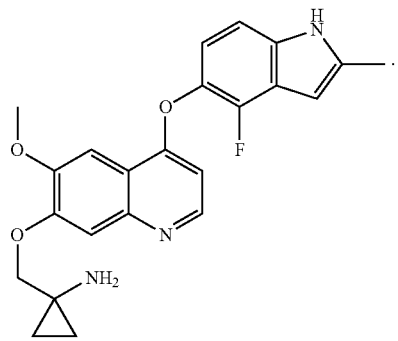

formula I

2. The therapeutic combination according to paragraph 1, wherein the pharmaceutically acceptable salt of the compound of formula I is 1-[[[4-(4-fluoro-2-methyl-1H-indol-5-yl)oxy-6-methoxyquinolin-7-yl]oxy]methyl]cyclopropylamine hydrochloride, preferably dihydrochloride.

3. The therapeutic combination according to paragraph 1 or 2, wherein the inhibitor for the interaction between PD-1 and its ligand PD-L1 is an anti-PD-1 or an anti-PD-L1 antibody or an antigen-binding fragment thereof.

4. The therapeutic combination according to paragraph 3, wherein the anti-PD-1 or anti-PD-L1 antibody is an anti-PD-1 or anti-PD-L1 monoclonal antibody.

5. The therapeutic combination according to paragraph 3 or 4, wherein the anti-PD-1 antibody is selected from any one or more of the group consisting of nivolumab, pembrolizumab, toripalimab, sintilimab, camrelizumab, tislelizumab, 14C12H1L1, genolimzumab, lizumab, HLX-10, BAT-1306, AK103, AK104, CS1003, SCT-I10A, F520, SG001 and GLS-010.

6. The therapeutic combination according to paragraph 3 or 4, wherein the anti-PD-L1 antibody is selected from any one or more of the group consisting of atezolizumab, avelumab, durvalumab, KL-A167, SHR-1316, BGB-333, JS003, STI-A1014 (ZKAB0011), KN035, MSB2311, HLX-20 and CS-1001.

7. The therapeutic combination according to paragraph 3 or 4, wherein the anti-PD-1 antibody comprises:
   a heavy chain variable region comprising an amino acid sequence selected from the group consisting of SEQ ID NO: 1, SEQ ID NO: 2, SEQ ID NO: 3, SEQ ID NO: 7, SEQ ID NO: 8, SEQ ID NO: 11, SEQ ID NO: 12, SEQ ID NO: 13, SEQ ID NO: 31, SEQ ID NO: 32 and SEQ ID NO 33 or an amino acid sequence having at least 80% identity thereto; and
   a light chain variable region comprising an amino acid sequence selected from the group consisting of SEQ ID NO: 4, SEQ ID NO: 5, SEQ ID NO: 6, SEQ ID NO: 9, SEQ ID NO: 10, SEQ ID NO: 14, SEQ ID NO: 15, SEQ ID NO: 16, SEQ ID NO: 34, SEQ ID NO: 35 and SEQ ID NO: 36 or an amino acid sequence having at least 80% identity thereto.

8. The therapeutic combination according to paragraph 7, wherein the anti-PD-1 antibody comprises:
   a. a heavy chain variable region set forth in SEQ ID NO: 1 and a light chain variable region set forth in SEQ ID NO: 4;
   b. a heavy chain variable region set forth in SEQ ID NO: 2 and a light chain variable region set forth in SEQ ID NO: 5;
   c. a heavy chain variable region set forth in SEQ ID NO: 3 and a light chain variable region set forth in SEQ ID NO: 6;
   d. a heavy chain variable region set forth in SEQ ID NO: 7 and a light chain variable region set forth in SEQ ID NO: 9;
   e. a heavy chain variable region set forth in SEQ ID NO: 8 and a light chain variable region set forth in SEQ ID NO: 10;
   f. a heavy chain variable region set forth in SEQ ID NO: 11 and a light chain variable region set forth in SEQ ID NO: 14;
   g. a heavy chain variable region set forth in SEQ ID NO: 12 and a light chain variable region set forth in SEQ ID NO: 15;
   h. a heavy chain variable region set forth in SEQ ID NO: 13 and a light chain variable region set forth in SEQ ID NO: 16;
   i. a heavy chain set forth in SEQ ID NO: 17 and a light chain set forth in SEQ ID NO: 18;
   j. a heavy chain variable region set forth in SEQ ID NO: 31 and a light chain variable region set forth in SEQ ID NO: 34;
   k. a heavy chain variable region set forth in SEQ ID NO: 32 and a light chain variable region set forth in SEQ ID NO: 35;
   l. a heavy chain variable region set forth in SEQ ID NO: 33 and a light chain variable region set forth in SEQ ID NO: 36;
   m. a heavy chain set forth in SEQ ID NO: 37 and a light chain set forth in SEQ ID NO: 40;
   n. a heavy chain set forth in SEQ ID NO: 38 and a light chain set forth in SEQ ID NO: 41; or
   o. a heavy chain set forth in SEQ ID NO: 39 and a light chain set forth in SEQ ID NO: 42.

9. The therapeutic combination according to any one of paragraphs 1-8, wherein the therapeutic combination is a fixed combination.

10. The therapeutic combination according to paragraph 9, wherein the fixed combination is in the form of a solid pharmaceutical composition or a liquid pharmaceutical composition.

11. The therapeutic combination according to any one of paragraphs 1-8, wherein the therapeutic combination is a non-fixed combination.

12. The therapeutic combination according to paragraph 11, wherein the anti-PD-1 antibody and the compound of formula I or the pharmaceutically acceptable salt thereof in the non-fixed combination are each in the form of a pharmaceutical composition.

13. The therapeutic combination according to any one of paragraphs 1-12, comprising: the compound of formula I or the hydrochloride thereof; and sintilimab or an antigen-binding fragment thereof, InVivoMAb anti-mouse PD-1 monoclonal antibody or an antigen-binding fragment thereof or 14C12H1L1 or an antigen-binding fragment thereof.

14. Use of the therapeutic combination according to any one of paragraphs 1-13 in treating or preventing a malignant liver tumor.

15. The use according to paragraph 14, wherein the therapeutic combination is used to treat primary liver tumor or secondary liver tumor.

16. The use according to paragraph 14, wherein the malignant liver tumor is liver parenchymal cell cancer.

17. The use according to paragraph 14, wherein the malignant liver tumor is metastatic liver cancer.

18. The use according to paragraph 17, wherein the metastatic liver cancer is a metastatic cancer metastasizing from lung cancer, gastric cancer, rectal cancer, colon cancer, colorectal cancer, pancreatic cancer, or breast cancer.

19. Use of an inhibitor for the interaction between PD-1 and its ligand PD-L1 in combination with a compound of formula I or a pharmaceutically acceptable salt thereof in preventing or treating cancer.

20. A therapeutic combination for the prevention or treatment of cancer or tumor, wherein the therapeutic combination comprises a compound of formula I or a pharmaceutically acceptable salt thereof and an inhibitor for the interaction between PD-1 and its ligand PD-L1.

21. The use of any one according to paragraphs 19-20, wherein the inhibitor for the interaction between PD-1 and its ligand PD-L1 is an anti-PD-1 or anti-PD-L1 monoclonal antibody or an antigen-binding fragment thereof specifically binding to human PD-1 or PD-L1 and blocking the binding of human PD-L1 to human PD-1.

22. The use of any one according to paragraphs 19-21, wherein the cancer or tumor is selected from a group consisting of liver tumor (e.g., a malignant liver tumor, such as hepatocellular carcinoma) and lung tumor (e.g., lung cancer, such as non-small cell lung cancer).

23. A method for treating cancer in an entity, comprising administering to the entity a therapeutically effective amount of a therapeutic combination comprising:
   an inhibitor for the interaction between PD-1 receptor and its ligand PD-L1, and
   a tyrosine kinase inhibitor, wherein the tyrosine kinase inhibitor is a compound of formula I or a pharmaceutically acceptable salt thereof.

24. The method according to paragraph 23, wherein the inhibitor for the interaction between PD-1 and its ligand PD-L1 is an anti-PD-1 or an anti-PD-L1 antibody or an antigen-binding fragment thereof.

25. The method according to paragraph 24, wherein the anti-PD-1 antibody is selected from any one or more of the group consisting of nivolumab, pembrolizumab, toripalimab, sintilimab, camrelizumab, tislelizumab, 14C12H1L1, genolimzumab, lizumab, HLX-10, BAT-1306, AK103, AK104, CS1003, SCT-I10A, F520, SG001 and GLS-010.

26. The method according to paragraph 24, wherein the anti-PD-L1 antibody is selected from any one or more of the group consisting of atezolizumab, avelumab, durvalumab, KL-A167, SHR-1316, BGB-333, JS003, STI-A1014, KN035, MSB2311, HLX-20 and CS-1001.

27. The method according to paragraph 24, wherein the anti-PD-1 antibody comprises:
   a heavy chain variable region comprising an amino acid sequence selected from the group consisting of SEQ ID NO: 1, SEQ ID NO: 2, SEQ ID NO: 3, SEQ ID NO: 7, SEQ ID NO: 8, SEQ ID NO: 11, SEQ ID NO: 12, SEQ ID NO: 13, SEQ ID NO: 31, SEQ ID NO: 32 and SEQ ID NO 33 or an amino acid sequence having at least 80% identity thereto; and
   a light chain variable region comprising an amino acid sequence selected from the group consisting of SEQ ID NO: 4, SEQ ID NO: 5, SEQ ID NO: 6, SEQ ID NO: 9, SEQ ID NO: 10, SEQ ID NO: 14, SEQ ID NO: 15, SEQ ID NO: 16, SEQ ID NO: 34, SEQ ID NO: 35 and SEQ ID NO: 36 or an amino acid sequence having at least 80% identity thereto.

28. The method according to any one of paragraphs 23-27, wherein the inhibitor for the interaction between PD-1 receptor and its ligand PD-L1 is administered about once a week (q1w), about once every 2 weeks (q2w), about once every 3 weeks (q3w), or about once every 4 weeks (q4w).

29. The method according to any one of paragraphs 23-28, wherein the method results in an objective response, preferably a complete response or a partial response.

30. The method according any one of paragraphs 23-29, wherein the entity has not previously received systemic chemotherapy.

31. The method according to any one of paragraphs 23-30, wherein the entity has not previously received systemic chemotherapy but has received one or more of surgical treatment, radiation therapy, induction chemotherapy, and/or adjuvant chemotherapy, or the entity has received concurrent chemotherapy.

32. The method according to any one of paragraphs 23-30, wherein the entity has previously received systemic chemotherapy.

33. The method according to any one of paragraphs 23-32, wherein the cancer is driver gene-negative.

34. The method according to paragraph 33, wherein the driver-gene negativity includes that 1, 2, or 3 of EGFR, ALK, and ROS1 genes of the entity are mutation-negative.

35. The method according to any one of paragraphs 26-32, wherein EGFR, ALK, and ROS1 genes in the entity are all wild-type genes or are all mutation-negative.

36. The method according to any one of paragraphs 26-35, wherein the cancer is lung cancer.

37. The method according to any one of paragraphs 23-36, wherein the cancer is recurrent and/or metastatic lung cancer.

38. The method according to any one of paragraphs 23-37, wherein the cancer is advanced lung cancer.

39. The method according to any one of paragraphs 23-38, wherein the cancer is small cell or non-small cell lung cancer.

40. The method according to any one of paragraphs 23-39, wherein the cancer treatment is a first-line treatment for recurrent or metastatic non-small cell lung cancer.

41. The method according to any one of paragraphs 39-40, wherein the non-small cell lung cancer is lung adenocarcinoma, squamous cell carcinoma of lung, or large cell lung carcinoma.

42. The method according to any one of paragraphs 26-35, wherein the cancer is primary liver tumor or secondary liver tumor.

43. The method according to paragraph 41, wherein the malignant liver tumor is a liver parenchymal cell cancer.

44. The method according to paragraph 41, wherein the malignant liver tumor is metastatic liver cancer.

45. The method according to paragraph 44, wherein the metastatic liver cancer is a metastatic cancer metastasizing from lung cancer, gastric cancer, rectal cancer, colon cancer, colorectal cancer, pancreatic cancer, or breast cancer.

46. A therapeutic combination for the prevention or treatment of cancer or tumor, wherein the therapeutic combination comprises a tyrosine kinase inhibitor and an inhibitor for the interaction between PD-1 and its ligand PD-L1, wherein the tyrosine kinase inhibitor is a compound of formula I or a pharmaceutically acceptable salt thereof.

47. The method or therapeutic combination according to any one of paragraphs 23-46, wherein the inhibitor for the interaction between PD-1 receptor and its ligand PD-L1 and the tyrosine kinase inhibitor are each in the form of a pharmaceutical composition and can be administered simultaneously, sequentially, or at intervals.

48. The method or therapeutic combination according to any one of paragraphs 23-47, wherein the compound of formula I or the pharmaceutically acceptable salt thereof is administered according to a treatment cycle of 2 weeks (14 days) of treatment plus 1 week (7 days) of interruption.

49. The method or therapeutic combination according to paragraph 48, wherein the therapeutic combination administered per treatment cycle comprises about 84-168 mg of the compound of formula I or the pharmaceutically acceptable salt thereof.

50. The method or therapeutic combination according to paragraph 48 or 49, wherein the therapeutic combination comprises an amount of the compound of formula I or the pharmaceutically acceptable salt thereof selected from the group consisting of about 84 mg, about 112 mg, about 140 mg, about 168 mg and a range formed by any of the aforementioned values.

51. The method or therapeutic combination according to paragraph 50, wherein the therapeutic combination comprises about 112 mg of the compound of formula I or the pharmaceutically acceptable salt thereof.

52. The method or therapeutic combination according to paragraph 50, wherein the therapeutic combination comprises about 140 mg of the compound of formula I or the pharmaceutically acceptable salt thereof.

53. The method or therapeutic combination according to paragraph 50, wherein the therapeutic combination comprises about 168 mg of the compound of formula I or the pharmaceutically acceptable salt thereof.

54. The method or therapeutic combination according to paragraph 50, wherein about 8 mg, about 10 mg or about 12 mg of the compound of formula I or the pharmaceutically acceptable salt thereof is administered daily for 2 weeks, followed by 1 week of interruption.

55. The method or therapeutic combination according to any one of paragraphs 23-54, wherein 100-600 mg of the anti-PD-1 antibody is administered about once every 2 weeks (q2w) or about once every 3 weeks (q3w).

56. The method or therapeutic combination according to any one of paragraphs 23-55, wherein about 200 mg of the anti-PD-1 antibody is administered about once every 2 weeks (q2w).

57. The method or therapeutic combination according to any one of paragraphs 23-56, wherein about 200 mg of the anti-PD-1 antibody is administered about once every 3 weeks (q3w).

58. A pharmaceutical pack comprising separately packaged pharmaceutical compositions in separate containers, wherein a pharmaceutical composition comprising a compound of formula I or a pharmaceutically acceptable salt thereof is contained in one container and a pharmaceutical composition comprising an inhibitor for the interaction between PD-1 receptor and its ligand PD-L1 is contained in another container.

59. The pharmaceutical pack according to paragraph 58, comprising 84-168 mg of the compound of formula I or the pharmaceutically acceptable salt thereof.

60. The pharmaceutical pack according to paragraph 59, comprising an amount of the compound of formula I or the pharmaceutically acceptable salt thereof selected from the group consisting of 84 mg, 112 mg, 140 mg, 168 mg and a range formed by any of the aforementioned values.

61. The pharmaceutical pack according to paragraph 60, comprising 112-168 mg of the compound of formula I or the pharmaceutically acceptable salt thereof.

62. A kit for treating liver tumor, comprising (a) a first pharmaceutical composition comprising an inhibitor for the interaction between PD-1 receptor and its ligand PD-L1 as an active ingredient; and (b) a second pharmaceutical composition comprising a compound of formula I or a pharmaceutically acceptable salt thereof as an active ingredient.

63. The kit according to paragraph 62, comprising 84-168 mg of the compound of formula I or the pharmaceutically acceptable salt thereof.

64. The kit according to paragraph 63, comprising an amount of the compound of formula I or the pharmaceutically acceptable salt thereof selected from the group consisting of 84 mg, 112 mg, 140 mg, 168 mg and a range formed by any of the aforementioned values.

65. The kit according to paragraph 64, comprising 112-168 mg of the compound of formula I or the pharmaceutically acceptable salt thereof.

66. A unit formulation, comprising: a compound component, 6-12 mg of a compound of formula I or a hydrochloride thereof; and an antibody component, 50-350 mg of an anti-PD-1 antibody or an antigen-binding fragment thereof, wherein the compound component and the antibody component are packaged separately.

67. A method for preventing or treating cancer or tumor, wherein one or more of the unit formulations according to paragraph 66 are administered to a subject in need.

68. The method according to paragraph 67, wherein the cancer or tumor is selected from a group consisting of liver tumor (e.g., a malignant liver tumor, such as hepatocellular carcinoma) and lung tumor (e.g., lung cancer, such as non-small cell lung cancer).

According to the content disclosed in the present application, the compositions and methods of the present application have been described in terms of preferred embodiments. However, it will be apparent to those skilled in the art that variations may be applied to the compositions and/or methods and the steps or the sequence of steps of the methods described herein without departing from the concept, spirit and scope of the present application. The disclosed content of all documents cited herein are hereby incorporated by reference to the extent that they provide exemplary, procedural and other details supplementary to those described herein.

The invention claimed is:

1. A therapeutic combination, comprising:
   a) an inhibitor for the interaction between PD-1 and its ligand PD-L1, wherein the inhibitor is an anti-PD-1 antibody or an antigen-binding fragment thereof, and wherein the anti-PD-1 antibody is sintilimab and
   b) a tyrosine kinase inhibitor, wherein the tyrosine kinase inhibitor is a compound of formula I or a pharmaceutically acceptable salt thereof,

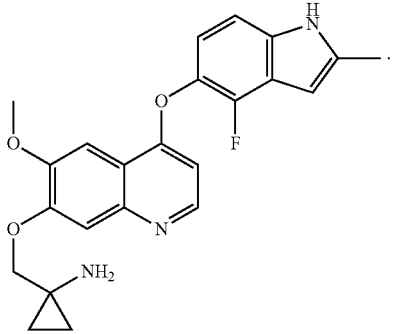

formula I

2. The therapeutic combination according to claim 1, wherein the pharmaceutically acceptable salt of the compound of formula I is 1-[[[4-(4-fluoro-2-methyl-1H-indol-5-yl)oxy-6-methoxyquinolin-7-yl]oxy]methyl]cyclopropylamine hydrochloride.

3. The therapeutic combination according to claim 1, comprising: a dihydrochloride of the compound of formula I; and sintilimab or an antigen-binding fragment thereof.

4. A method for treating cancer in an entity, comprising administering to the entity the therapeutically effective amount of a therapeutic combination according to claim 1, wherein the cancer is non-small cell lung cancer.

5. The method according to claim 4, wherein the anti-PD-1 antibody is administered about once a week (q1w), about once every 2 weeks (q2w), about once every 3 weeks (q3w), or about once every 4 weeks (q4w).

6. The method according to claim 4, wherein the non-small cell lung cancer is driver gene-negative.

7. The method according to claim 6, wherein 1, 2 or 3 of EGFR, ALK and ROS1 genes are mutation-negative.

8. The method according to claim 6, wherein the cancer is recurrent and/or metastatic non-small cell lung cancer or locally advanced non-small cell lung cancer.

9. The method according to claim 4, wherein the method is a first-line treatment for recurrent or metastatic non-small cell lung cancer.

10. The method according to claim 8, wherein the non-small cell lung cancer is lung adenocarcinoma, squamous cell carcinoma of lung, or large cell lung carcinoma.

11. The method according to claim 4, wherein the compound of formula I or the pharmaceutically acceptable salt thereof is administered according to a treatment cycle of 2 weeks (14 days) of treatment plus 1 week (7 days) of interruption.

12. The method according to claim 4, wherein the therapeutic combination administered per treatment cycle comprises about 84-168 mg of the compound of formula I or the pharmaceutically acceptable salt thereof.

13. The method according to claim 4, wherein 100-600 mg of the anti-PD-1 antibody is administered about once every 2 weeks (q2w) or about once every 3 weeks (q3w).

14. The method according to claim 4, wherein the anti-PD-1 antibody or the antigen-binding fragment thereof and the tyrosine kinase inhibitor are each in the form of a pharmaceutical composition and can be administered simultaneously, sequentially, or at intervals.

* * * * *

SEQUENCE LISTING

<160> NUMBER OF SEQ ID NOS: 42

<210> SEQ ID NO 1
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Gly Met Ser Trp Val Arg Gln Thr Pro Glu Lys Ser Leu Glu Trp Val
            35                  40                  45

Ala Thr Ile Ser Gly Gly Gly Ser Asp Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gln Leu Asn Tyr Ala Trp Phe Ala Tyr Trp Gly Gln Gly Thr
            100                 105                 110

Leu Val Thr Val Ser Ala Ala Lys Thr Thr Pro Pro Ser Val Tyr Arg
        115                 120                 125

Ser Ser Lys Gly Asn Ser Ser Thr Leu Ala Ala Val Thr Ser
    130                 135                 140

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Ser Ser Leu Arg Ala Glu Asp Thr Ala Val Tyr Tyr Cys
                85                  90                  95

Ala Arg Gln Leu Asn Tyr Ala Trp Phe Ala Tyr Trp Gly Gln Gly Thr
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Asn Tyr Ala Trp Phe Ala Tyr Trp Gly Gln Gly Thr
            100                 105                 110

Leu Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
```

```
                35                  40                  45
Lys Leu Leu Ile Tyr Thr Ser Ser Asn Gln Gly Ser Gly Val Pro Ala
        50                  55                  60

Arg Phe Ser Gly Ser Gly Ser Gly Thr Asp Phe Ser Leu Asn Ile His
65                  70                  75                  80

Pro Met Glu Glu Asp Thr Ala Met Tyr Phe Cys Gln Gln Ser Lys
                85                  90                  95

Glu Val Pro Trp Thr Phe Gly Gly Gly Thr Lys Leu Gly Ile Lys Arg
            100                 105                 110

<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Thr Ser Ser Asn Gln Gly Thr Gly Val Pro Ala
        50                  55                  60

Arg Phe Ser Gly Ser Gly Ser Gly Thr Asp Phe Thr Leu Asn Ile Asn
65                  70                  75                  80

Pro Met Glu Ala Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Tyr Gln Gln Lys Pro Gly Gln Pro Pro
        35                  40                  45

Lys Leu Leu Ile Tyr Thr Ser Ser Asn Lys Asp Thr Gly Val Pro Ala
        50                  55                  60

Arg Phe Ser Gly Ser Gly Ser Gly Thr Asp Phe Thr Leu Thr Ile Asn
65                  70                  75                  80

Pro Met Glu Ala Glu Asp Thr Ala Val Tyr Tyr Cys Gln Gln Ser Lys
                85                  90                  95

Glu Val Pro Trp Thr Phe Gly Gly Gly Thr Lys Leu Glu Ile Lys
            100                 105                 110
```

```
<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Asp Met Ser Trp Val Arg Gln Thr Pro Glu Lys Arg Leu Glu Trp Val
            35                  40                  45

Ala Thr Ile Ser Gly Gly Gly Arg Tyr Thr Tyr Tyr Pro Asp Ser Val
        50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ala
            115

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
                20                  25                  30

Asp Met Ser Trp Val Arg Gln Ala Pro Gly Lys Gly Leu Asp Trp Val
            35                  40                  45

Ala Thr Ile Ser Gly Gly Gly Arg Tyr Thr Tyr Tyr Pro Asp Ser Val
        50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                85                  90                  95

Ala Asn Arg Tyr Gly Glu Ala Trp Phe Ala Tyr Trp Gly Gln Gly Thr
            100                 105                 110

Leu Val Thr Val Ser Ser
            115

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

```
Asp Ile Lys Met Thr Gln Ser Pro Ser Ser Met Tyr Ala Ser Leu Gly
1               5                   10                  15

Glu Arg Val Thr Phe Thr Cys Lys Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu
            100                 105
```

```
<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Asp Ile Gln Met Thr Gln Ser Pro Ser Ser Met Ser Ala Ser Val Gly
1               5                   10                  15

Asp Arg Val Thr Phe Thr Cys Arg Ala Ser Gln Asp Ile Asn Thr Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Ser Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Met Ala Thr Tyr Tyr Cys Leu Gln Tyr Asp Glu Phe Pro Leu
                85                  90                  95

Thr Phe Gly Ala Gly Thr Lys Leu Glu Leu Lys
            100                 105
```

```
<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

```
Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Gly Leu Asp Trp Val
        35                  40                  45

Ala Thr Ile Ser Gly Gly Gly Arg Asp Thr Tyr Tyr Pro Asp Ser Val
50                  55                  60

Lys Gly Arg Phe Thr Ile Ser Arg Asp Asn Ser Lys Asn Asn Leu Tyr
65                  70                  75                  80
```

```
Leu Gln Met Asn Ser Leu Arg Ala Glu Asp Thr Ala Leu Tyr Tyr Cys
                 85                  90                  95

Ala Arg Gln Lys Gly Glu Ala Trp Phe Ala Tyr Trp Gly Gln Gly Thr
            100                 105                 110

Leu Val Thr Val Ser Ser
        115

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Leu Tyr Tyr Cys
                 85                  90                  95

Ala Arg Gln Lys Gly Glu Ala Trp Phe Ala Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Gln Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Ala Pro Gly Lys Gly Leu Asp Trp Val
        35                  40                  45

Ala Thr Ile Ser Gly Gly Gly Arg Asp Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Gln Lys Gly Glu Ala Trp Phe Ala Tyr Trp Gly Gln Gly Thr
            100                 105                 110

Leu Val Thr Val Ser Ser
        115
```

```
<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile His
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Leu Thr Gln Ser Pro Ala Ser Leu Ala Val Ser Pro Gly
1               5                   10                  15
```

```
Gln Arg Ala Thr Ile Thr Cys Arg Ala Ser Glu Ser Val Asp Asn Tyr
             20                  25                  30

Gly Ile Ser Phe Met Asn Trp Tyr Gln Gln Lys Pro Gly Gln Pro Pro
         35                  40                  45

Lys Leu Leu Ile Tyr Ala Ala Ser Asn Lys Ala Thr Gly Val Pro Ala
 50                  55                  60

Arg Phe Ser Gly Ser Gly Ser Gly Thr Asp Phe Thr Leu Asn Ile Asn
 65                  70                  75                  80

Pro Met Glu Ala Asn Asp Thr Ala Val Tyr Phe Cys Gln Gln Ser Lys
                 85                  90                  95

Glu Val Pro Trp Thr Phe Gly Gly Gly Thr Lys Leu Glu Ile Lys
            100                 105                 110
```

<210> SEQ ID NO 17
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Glu Val Gln Leu Val Gln Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
             20                  25                  30

Gly Met Ser Trp Val Arg Gln Ala Pro Gly Lys Gly Leu Asp Trp Val
         35                  40                  45

Ala Thr Ile Ser Gly Gly Gly Arg Asp Thr Tyr Tyr Pro Asp Ser Val
 50                  55                  60

Lys Gly Arg Phe Thr Ile Ser Arg Asp Asn Ser Lys Asn Asn Leu Tyr
 65                  70                  75                  80

Leu Gln Met Asn Ser Leu Arg Ala Glu Asp Thr Ala Leu Tyr Tyr Cys
                 85                  90                  95

Ala Arg Gln Lys Gly Glu Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Arg Thr Pro Glu Val
                245                 250                 255

Thr Cys Val Val Val Asp Val Ser Gln Glu Asp Pro Glu Val Gln Phe
            260                 265                 270
```

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His His Tyr Thr
            420                 425                 430

Gln Lys Ser Leu Ser Leu Ser Leu Gly Lys
            435                 440

<210> SEQ ID NO 18
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Lys Gly Thr Gly Val Pro Ala
    50                  55                  60

Arg Phe Ser Gly Ser Gly Ser Gly Thr Asp Phe Thr Leu Asn Ile Asn
65                  70                  75                  80

Pro Met Glu Glu Asn Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys

```
                180                 185                 190
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Phe Thr Phe Ser Ser Tyr Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ile Ser Gly Gly Gly Ser Asp Thr
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Arg Gln Leu Asn Tyr Ala Trp Phe Ala Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Ser Val Asp Asn Tyr Gly Ile Ser Phe
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr Ser Ser
1
```

```
<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Gln Ser Lys Glu Val Pro Trp Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Phe Ala Phe Ser Ser Tyr Asp
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ile Ser Gly Gly Gly Arg Tyr Thr
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Asn Arg Tyr Gly Glu Ala Trp Phe Ala Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Asp Ile Asn Thr Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

Arg Ala Asn
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Gln Tyr Asp Glu Phe Pro Leu Thr
1               5

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120

<210> SEQ ID NO 32
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

```
Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser
```

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115
```

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

<210> SEQ ID NO 35
<211> LENGTH: 107
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 37
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45
```

```
Gly Gly Ile Asn Pro Ser Asn Gly Gly Thr Asn Phe Asn Glu Lys Phe
         50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
                260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
        435                 440                 445

<210> SEQ ID NO 38
<211> LENGTH: 440
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Gln Val Gln Leu Val Glu Ser Gly Gly Gly Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380
```

```
Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 39
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Arg Asp Thr Tyr Phe Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
```

```
            290                 295                 300
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440
```

<210> SEQ ID NO 40
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215
```

<210> SEQ ID NO 41
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 42
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60
```

```
Ser Gly Ser Gly Thr Asp Phe Thr Leu Thr Ile Arg Thr Leu Gln Pro
 65                  70                  75                  80

Glu Asp Phe Ala Thr Tyr Tyr Cys Gln Gln Ser Ser Asn Thr Pro Phe
                 85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```